US 10,952,884 B2

(12) United States Patent
Shalev

(10) Patent No.: US 10,952,884 B2
(45) Date of Patent: Mar. 23, 2021

(54) MULTI-FABRIC ENDOVASCULAR STENT-GRAFT

(71) Applicant: ENDOSPAN LTD., Herzilyia Pituach (IL)

(72) Inventor: Alon Shalev, Raanana (IL)

(73) Assignee: ENDOSPAN LTD., Herzilyia (IL)

(*) Notice: Subject to any disclaimer, the term of this patent is extended or adjusted under 35 U.S.C. 154(b) by 282 days.

(21) Appl. No.: 15/976,317

(22) Filed: May 10, 2018

(65) Prior Publication Data
US 2018/0256377 A1 Sep. 13, 2018

Related U.S. Application Data

(63) Continuation of application No. 14/759,736, filed as application No. PCT/IL2014/050019 on Jan. 7, 2014, now Pat. No. 9,993,360.
(Continued)

(51) Int. Cl.
*A61F 2/962* (2013.01)
*A61F 2/07* (2013.01)
(Continued)

(52) U.S. Cl.
CPC ............... *A61F 2/962* (2013.01); *A61F 2/07* (2013.01); *A61F 2/966* (2013.01);
(Continued)

(58) Field of Classification Search
CPC .... A61F 2/90; A61F 2250/0063; A61F 2/852; A61F 2230/0054; A61F 2/89;
(Continued)

(56) References Cited

U.S. PATENT DOCUMENTS 5,575,818 A 11/1996 Pinchuk
5,609,627 A 3/1997 Goicoechea et al.
(Continued)

FOREIGN PATENT DOCUMENTS

CN 202122626 U 1/2012
CN 102813969 A 12/2012
(Continued)

OTHER PUBLICATIONS

English Summary of an Office Action issued in corresponding Chinese Appl. No. 201710222239.7, dated Sep. 29, 2018.
(Continued)

*Primary Examiner* — Katherine M Shi
(74) *Attorney, Agent, or Firm* — Sughrue Mion, PLLC

(57) ABSTRACT

An endovascular stent-graft is provided that includes a flexible stent member and a tubular fluid flow guide. The tubular fluid flow guide includes first and second fabrics. The first fabric includes a first biologically-compatible substantially blood-impervious material, and is attached to and covers the stent member along a first longitudinal portion of the stent-graft. The second fabric includes a second biologically-compatible substantially blood-impervious material different from the first material, and is attached to and covers the stent member along a second longitudinal portion of the stent-graft. The second longitudinal portion is at least partially non-longitudinally-overlapping with the first longitudinal portion. Other embodiments are also described.

21 Claims, 24 Drawing Sheets

Related U.S. Application Data

(60) Provisional application No. 61/749,965, filed on Jan. 8, 2013.

(51) Int. Cl.
*A61F 2/966* (2013.01)
*A61F 2/06* (2013.01)

(52) U.S. Cl.
CPC ... *A61F 2002/061* (2013.01); *A61F 2002/067* (2013.01); *A61F 2002/075* (2013.01); *A61F 2002/9665* (2013.01); *A61F 2230/0069* (2013.01)

(58) Field of Classification Search
CPC ........ A61F 2002/072; A61F 2210/0076; A61F 2230/0069; A61F 2230/008; A61F 2250/0039; A61F 2/856; A61F 2002/065; A61F 2002/823; A61F 2/06; A61F 2002/061; A61F 2002/067; A61F 2002/075; A61F 2002/9665; A61F 2/07; A61F 2/962; A61F 2/966
See application file for complete search history.

(56) References Cited

U.S. PATENT DOCUMENTS

| | | | |
|---|---|---|---|
| 5,628,788 | A | 5/1997 | Pinchuk |
| 5,653,743 | A | 8/1997 | Marin |
| 6,030,415 | A | 2/2000 | Chuter |
| 6,368,345 | B1 | 4/2002 | Dehdashtian et al. |
| 6,613,078 | B1 | 9/2003 | Barone |
| 6,814,752 | B1 | 11/2004 | Chuter |
| 7,083,822 | B2 | 8/2006 | Brightbill |
| 7,887,575 | B2 | 2/2011 | Kujawski |
| 8,540,764 | B2 | 9/2013 | Bruszewski et al. |
| 9,993,360 | B2 | 6/2018 | Shalev et al. |
| 2002/0052643 | A1 | 5/2002 | Wholey et al. |
| 2004/0034403 | A1 | 2/2004 | Schmitt |
| 2004/0117003 | A1 | 6/2004 | Ouriel et al. |
| 2006/0095118 | A1* | 5/2006 | Hartley ............ A61F 2/89 623/1.35 |
| 2006/0100684 | A1 | 5/2006 | Elliott |
| 2009/0099649 | A1* | 4/2009 | Chobotov ......... A61F 2/966 623/1.36 |
| 2010/0063575 | A1 | 3/2010 | Shalev et al. |
| 2010/0082091 | A1 | 4/2010 | Berez et al. |
| 2011/0093002 | A1 | 4/2011 | Rucker et al. |
| 2012/0150274 | A1 | 6/2012 | Shalev et al. |
| 2012/0179236 | A1 | 7/2012 | Benary et al. |
| 2012/0310319 | A1 | 12/2012 | Tieu et al. |
| 2013/0172984 | A1* | 7/2013 | Greenberg ......... A61F 2/07 623/1.24 |
| 2014/0188207 | A1* | 7/2014 | Havel ............... A61F 2/07 623/1.11 |
| 2015/0351943 | A1 | 12/2015 | Shalev et al. |

FOREIGN PATENT DOCUMENTS

| | | |
|---|---|---|
| EP | 1621159 | 2/2006 |
| EP | 1779809 | 5/2007 |
| WO | 00/028923 | 5/2000 |
| WO | 2005/046524 A1 | 5/2005 |
| WO | 2006/028925 A1 | 3/2006 |
| WO | 2006/088905 A1 | 8/2006 |
| WO | 2006/130755 A2 | 12/2006 |
| WO | 2008/021557 A1 | 2/2008 |
| WO | 2009104000 A1 | 8/2009 |
| WO | 2011/064782 | 6/2011 |
| WO | 2011064782 A2 | 6/2011 |
| WO | 2013/030819 | 3/2013 |

OTHER PUBLICATIONS

An Office Action dated Mar. 8, 2019, which issued during the prosecution of Canadian Patent Application No. 3009244.
U.S. Appl. No. 61/749,965, filed Jan. 8, 2013.
An English translation of an Office Action dated Jun. 10, 2019, which issued during the prosecution of Chinese Patent Application No. 201710222239.7.
Criado 2000 Endovascular Management of Aortic Aneurysm Chapter from Aortic Surgery.

* cited by examiner

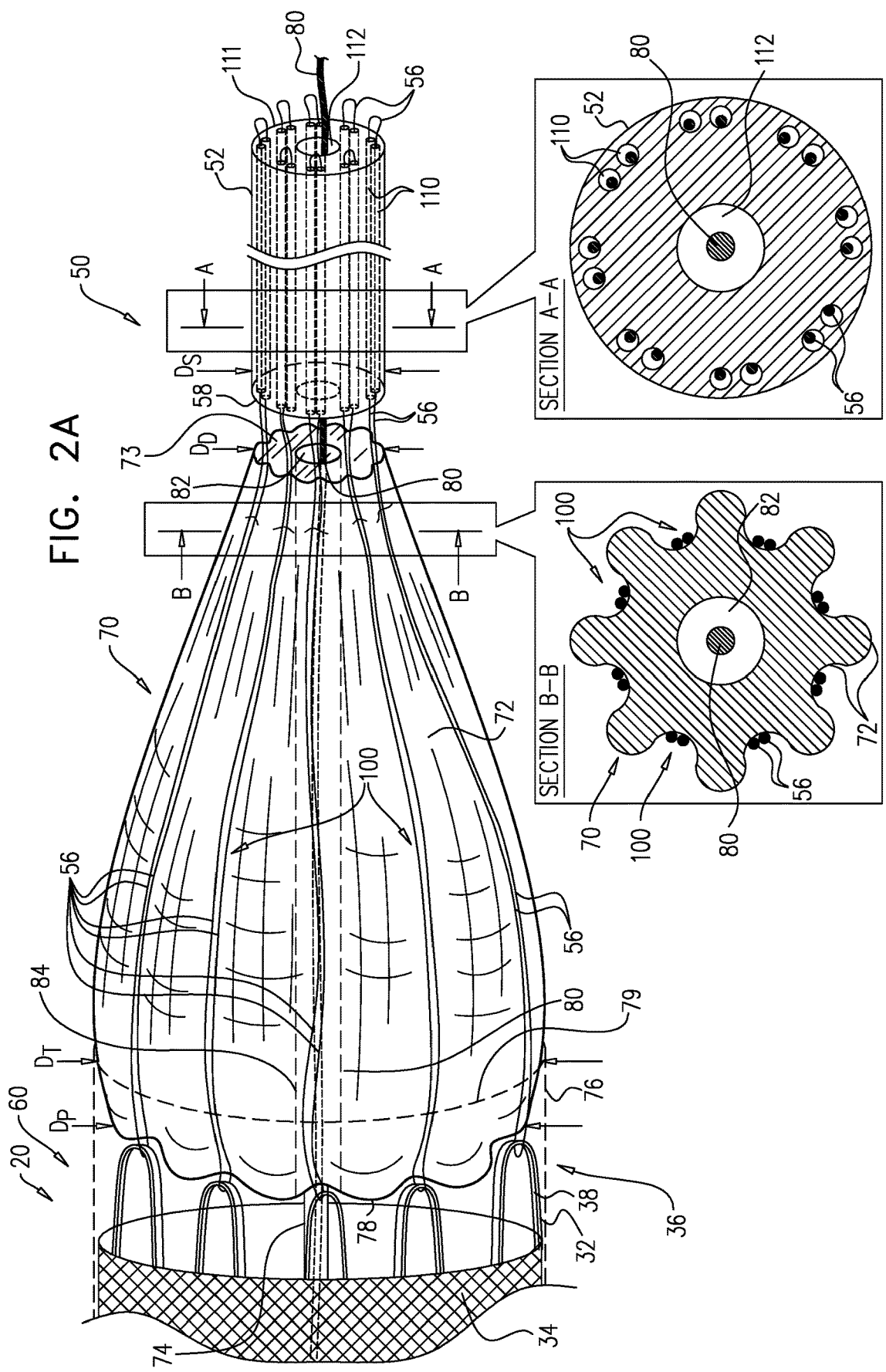

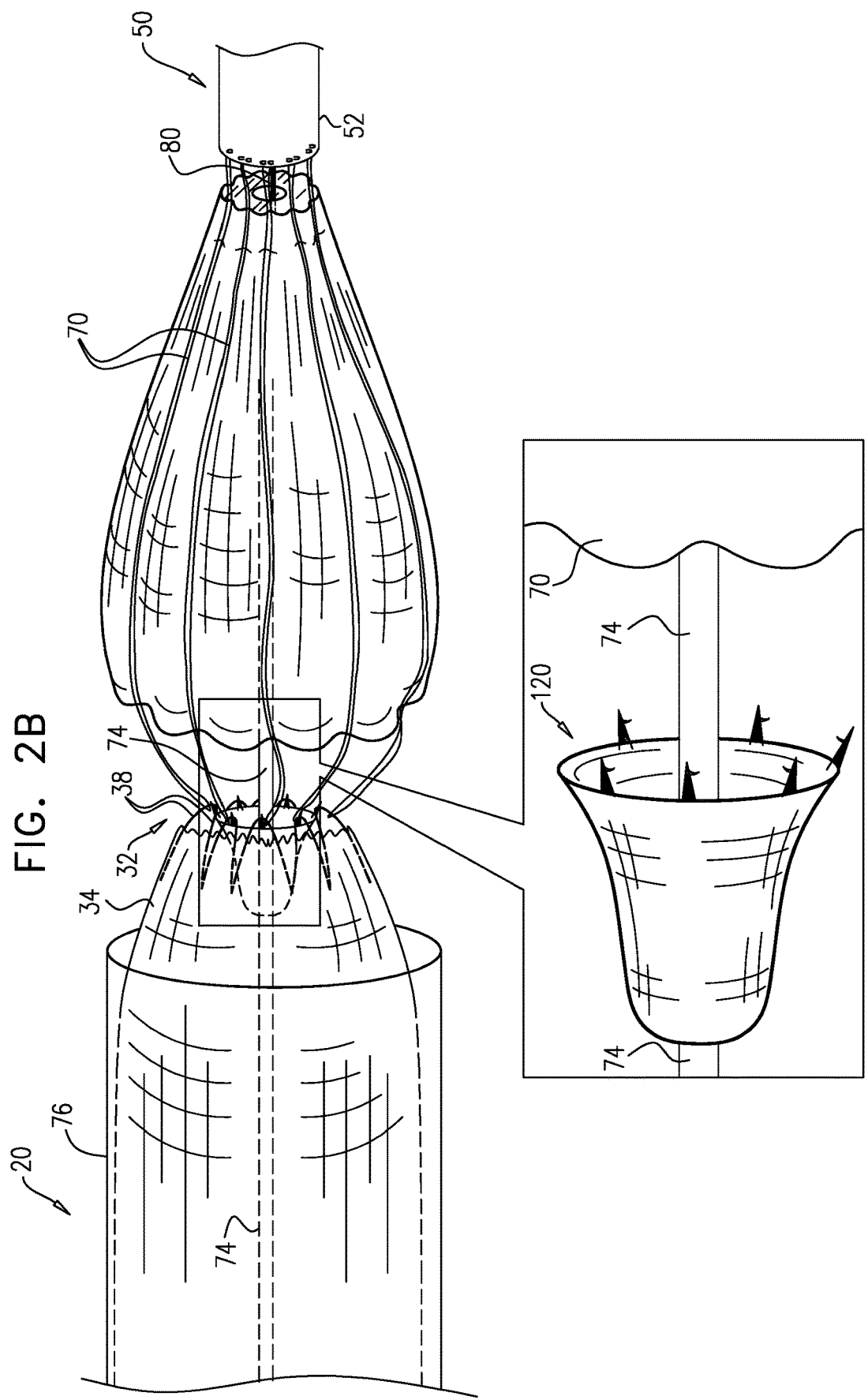

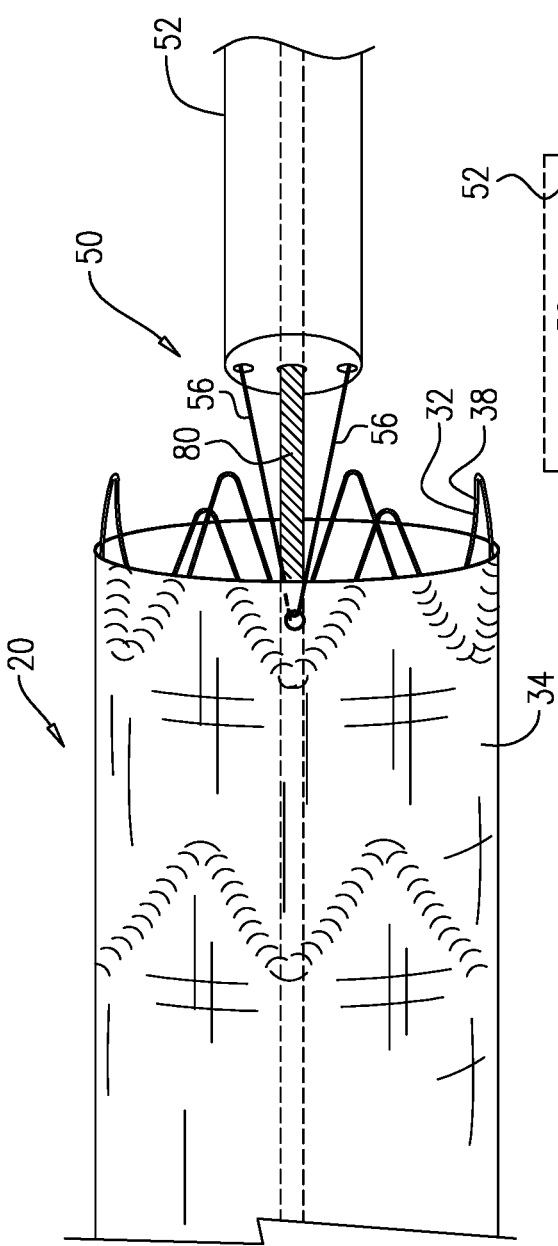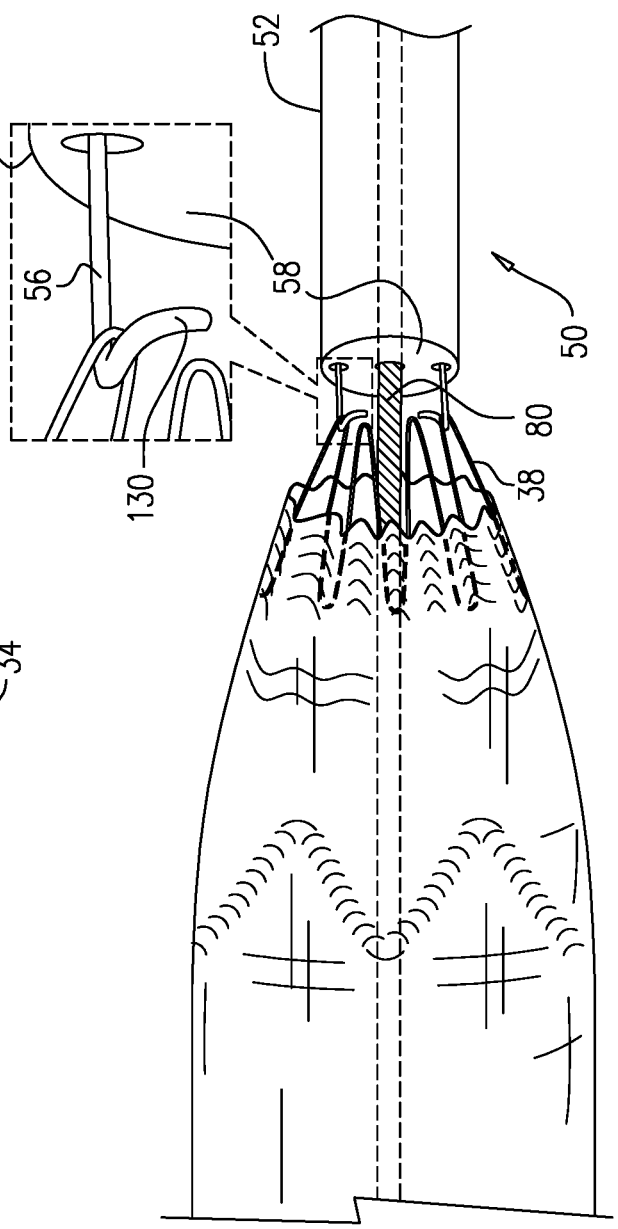

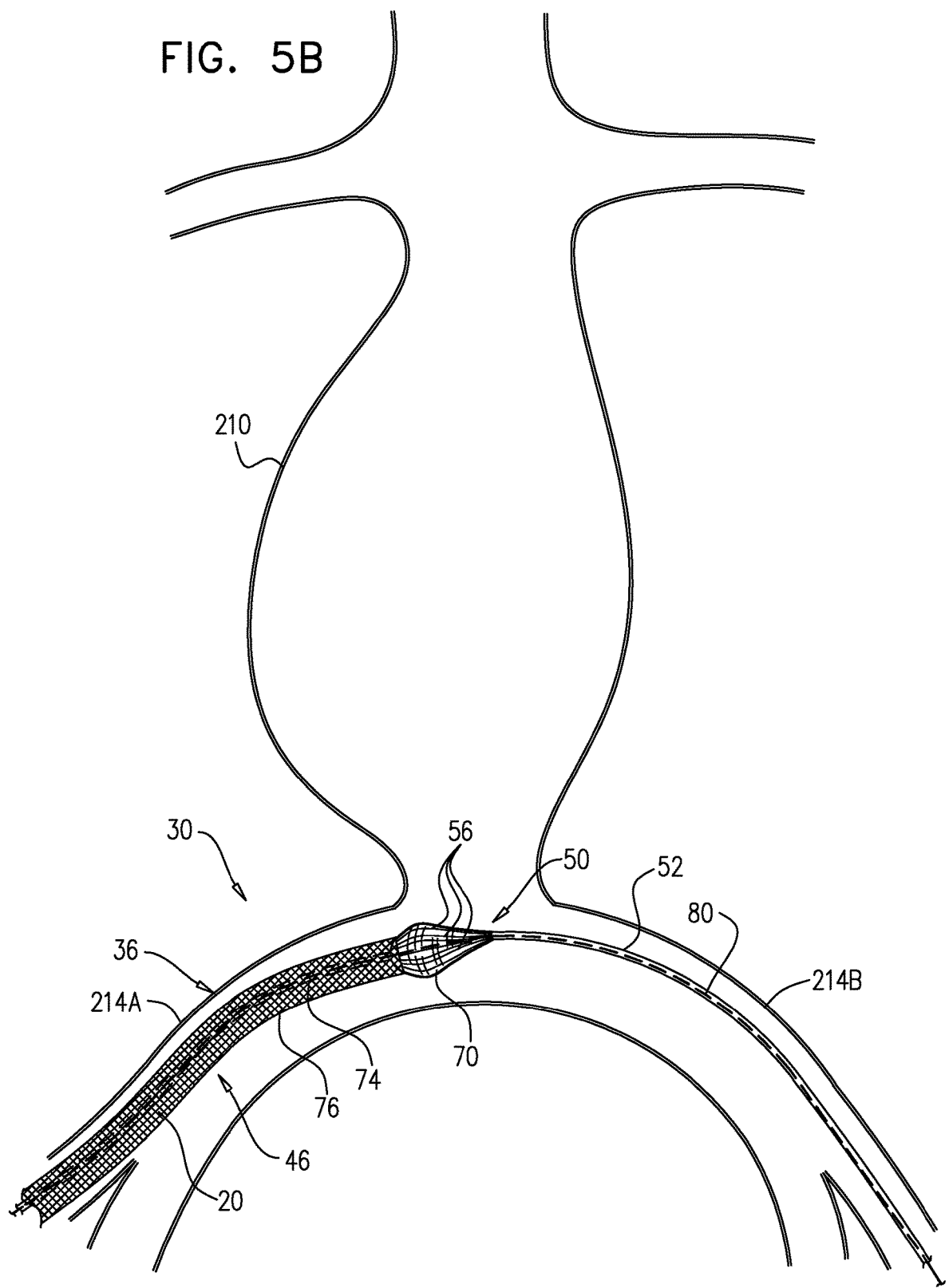

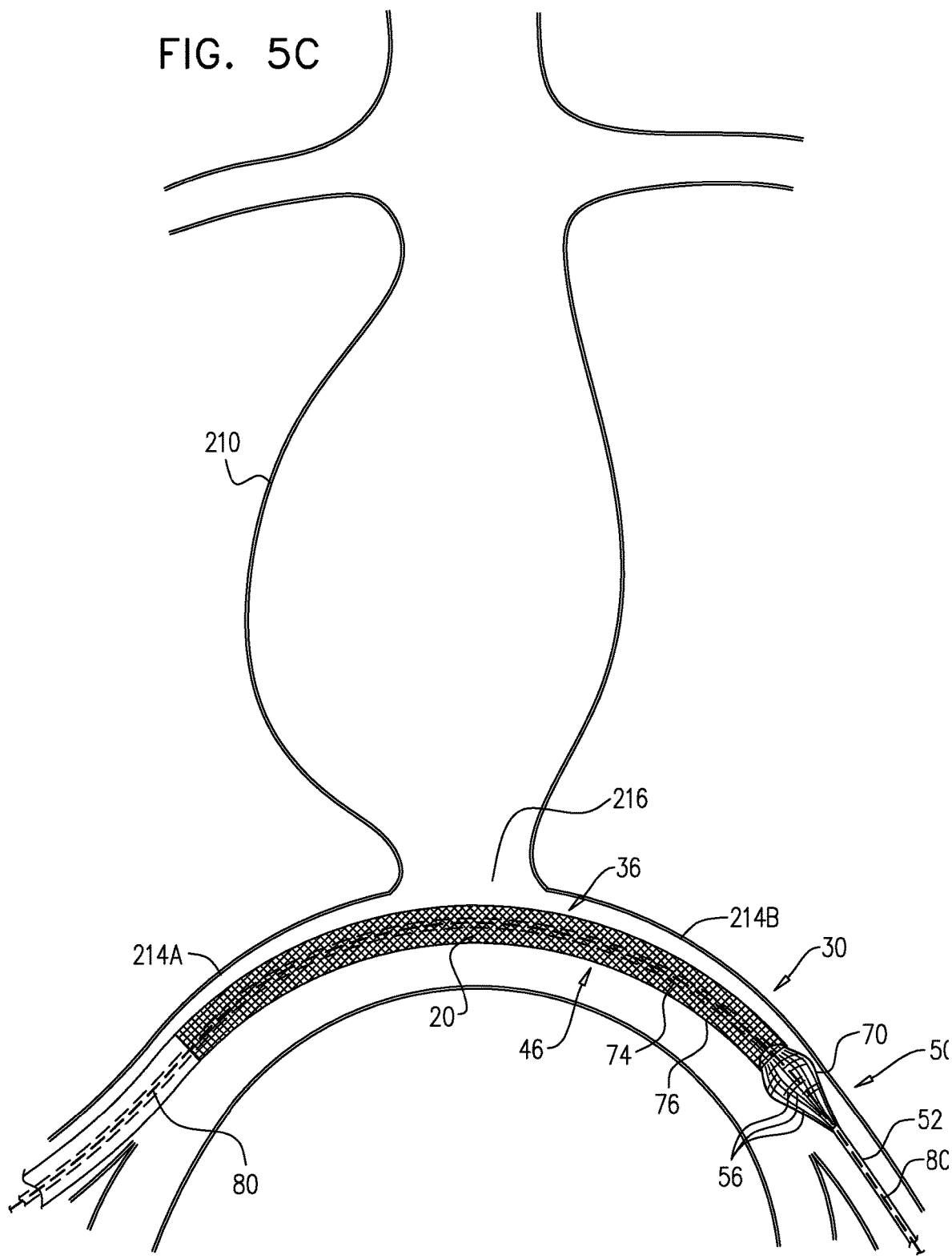

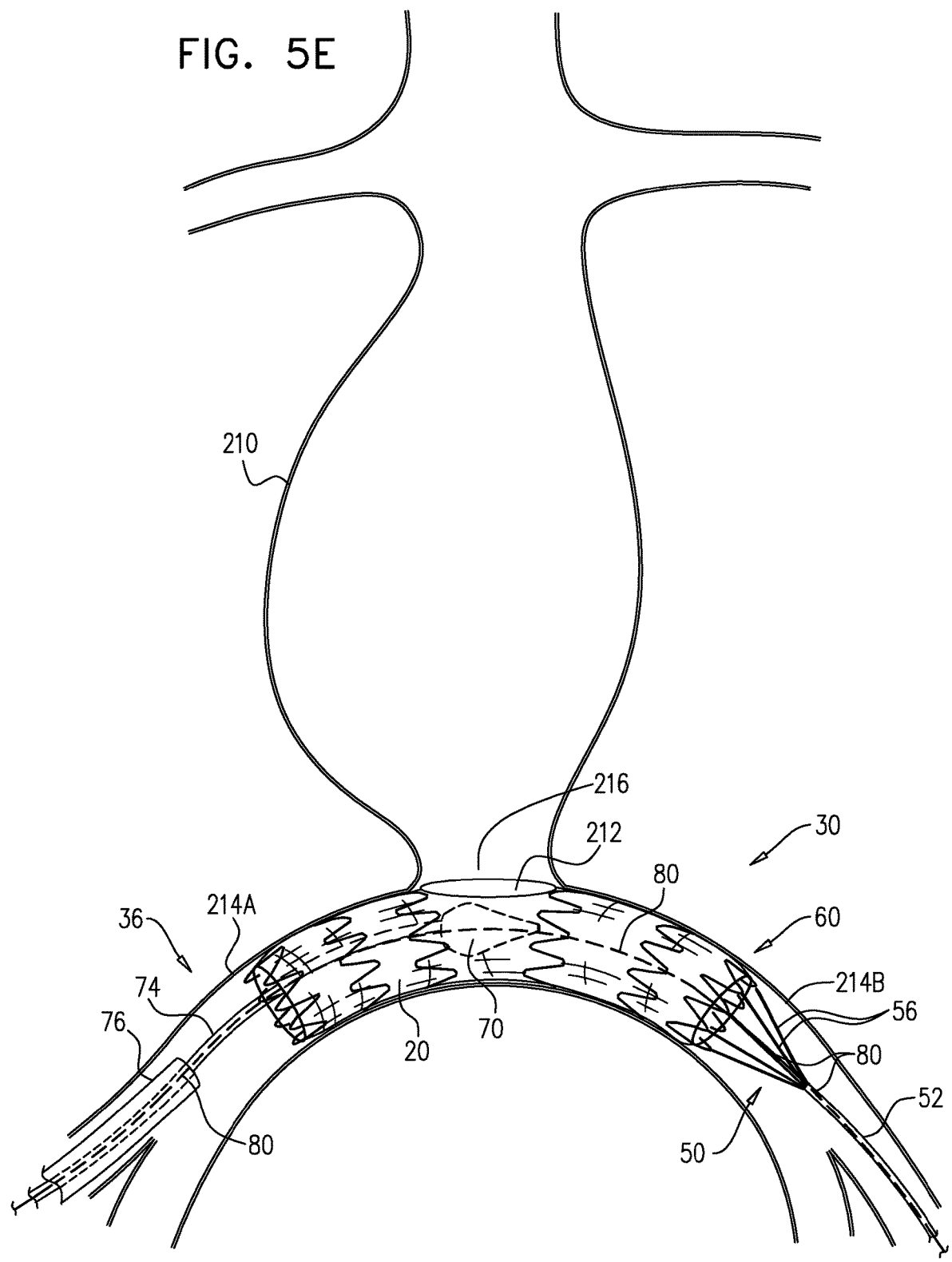

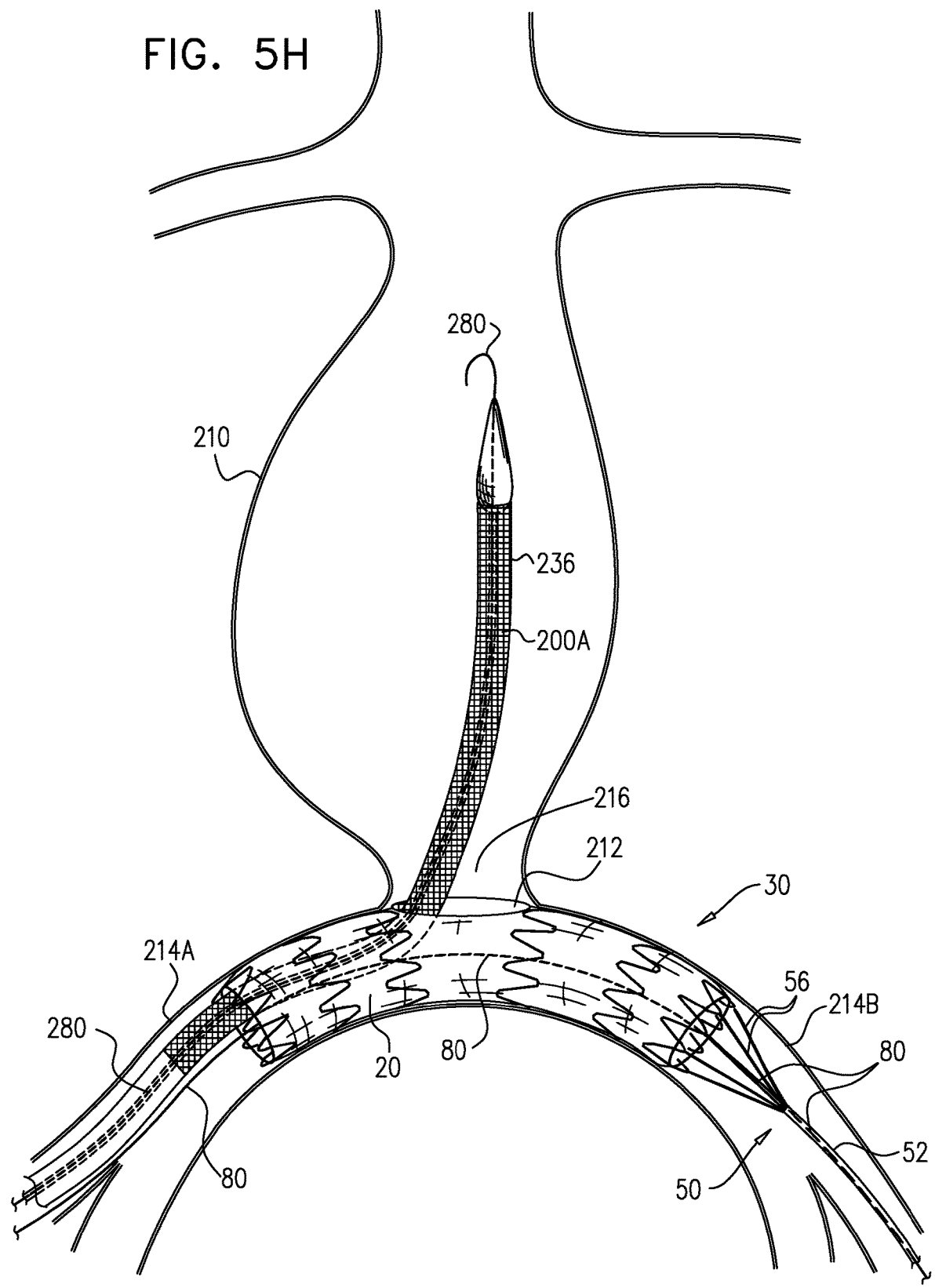

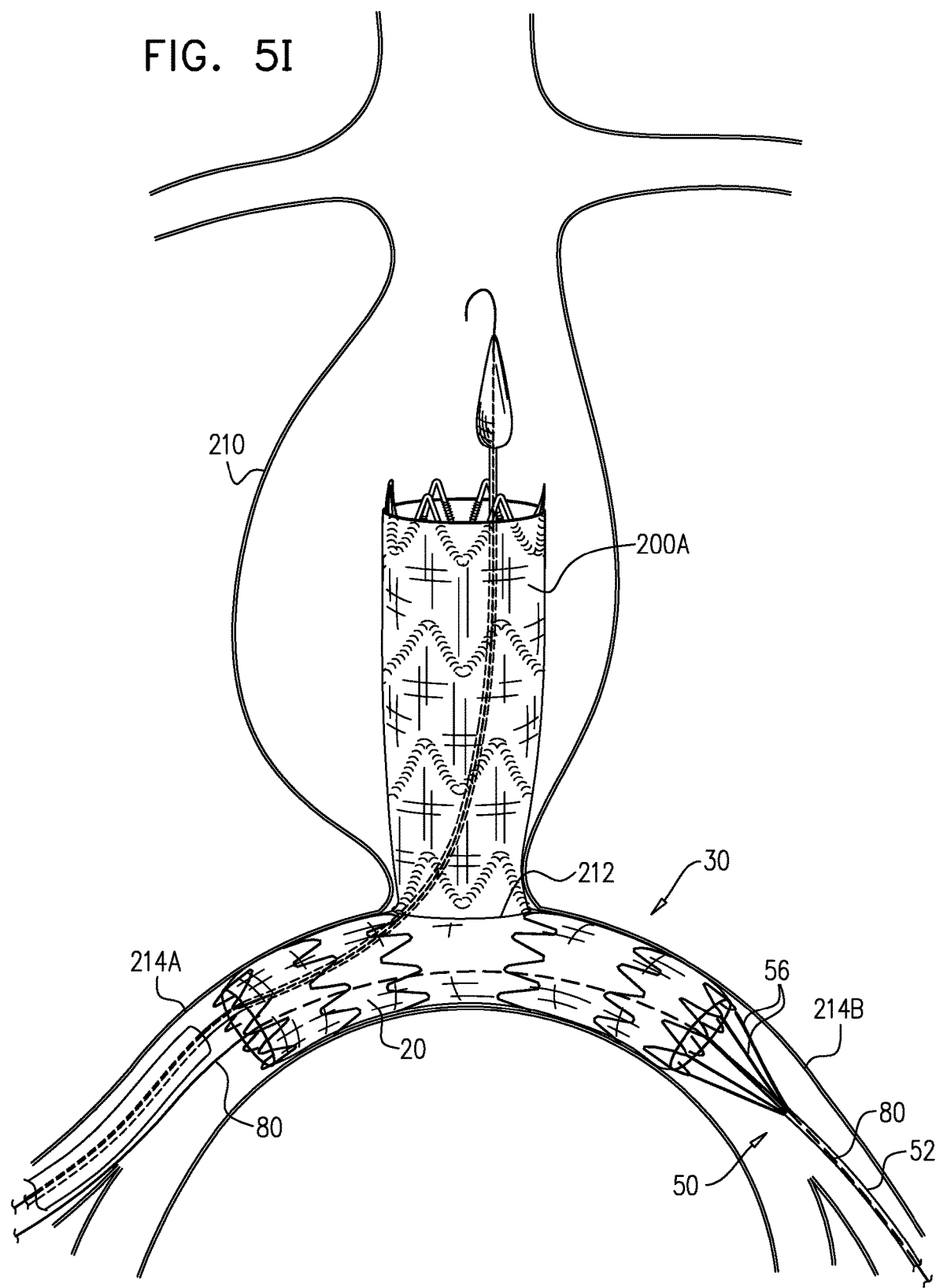

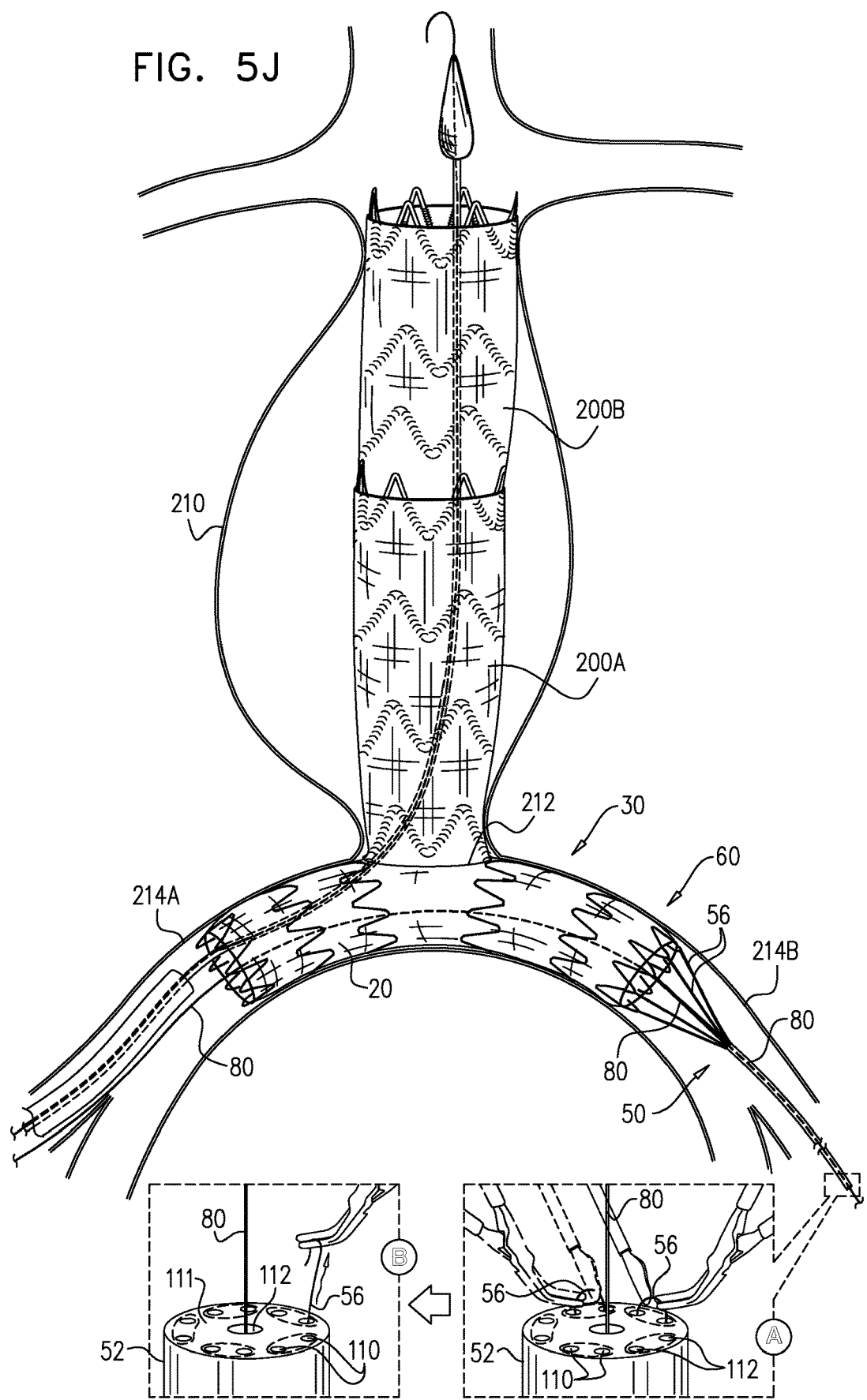

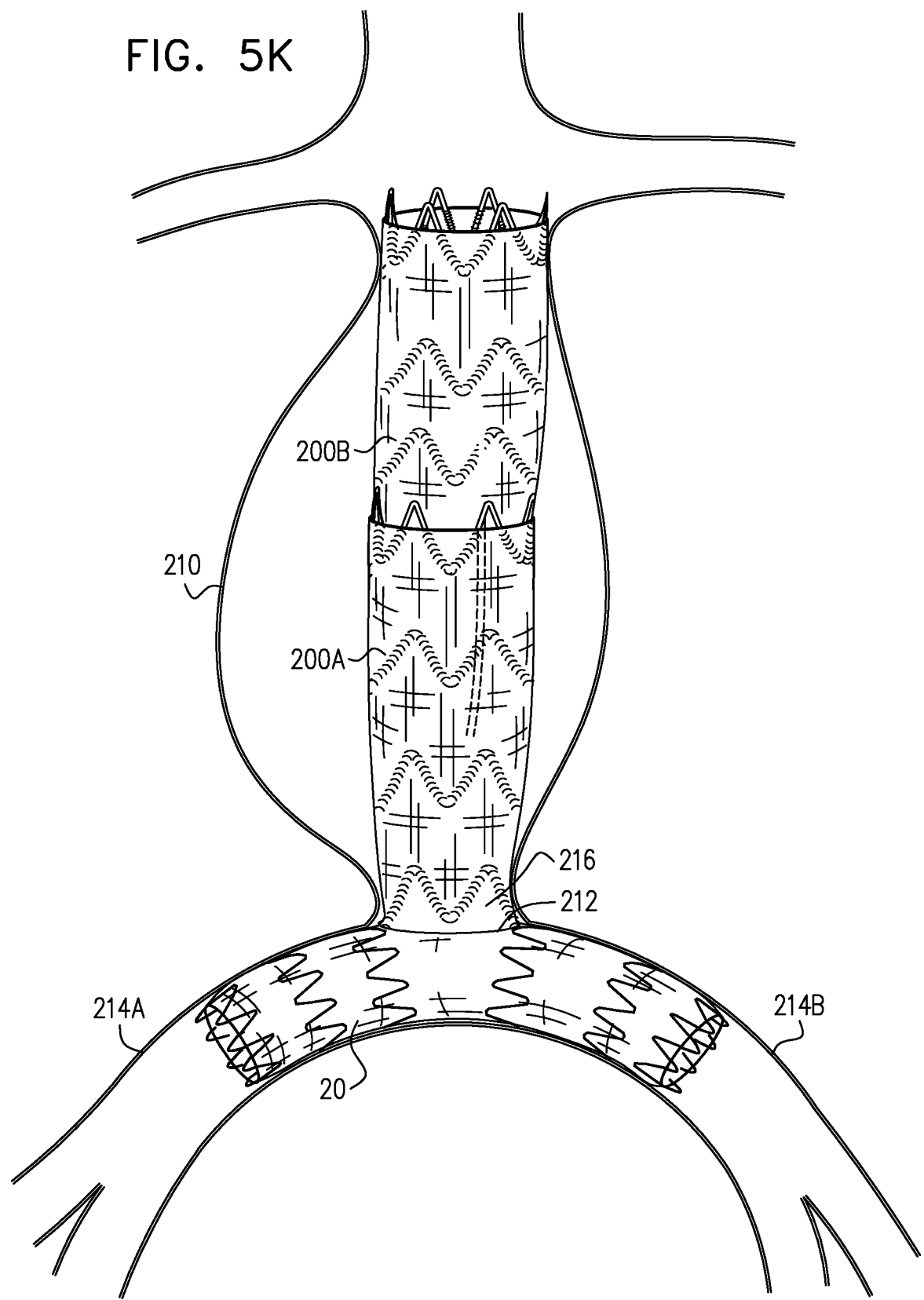

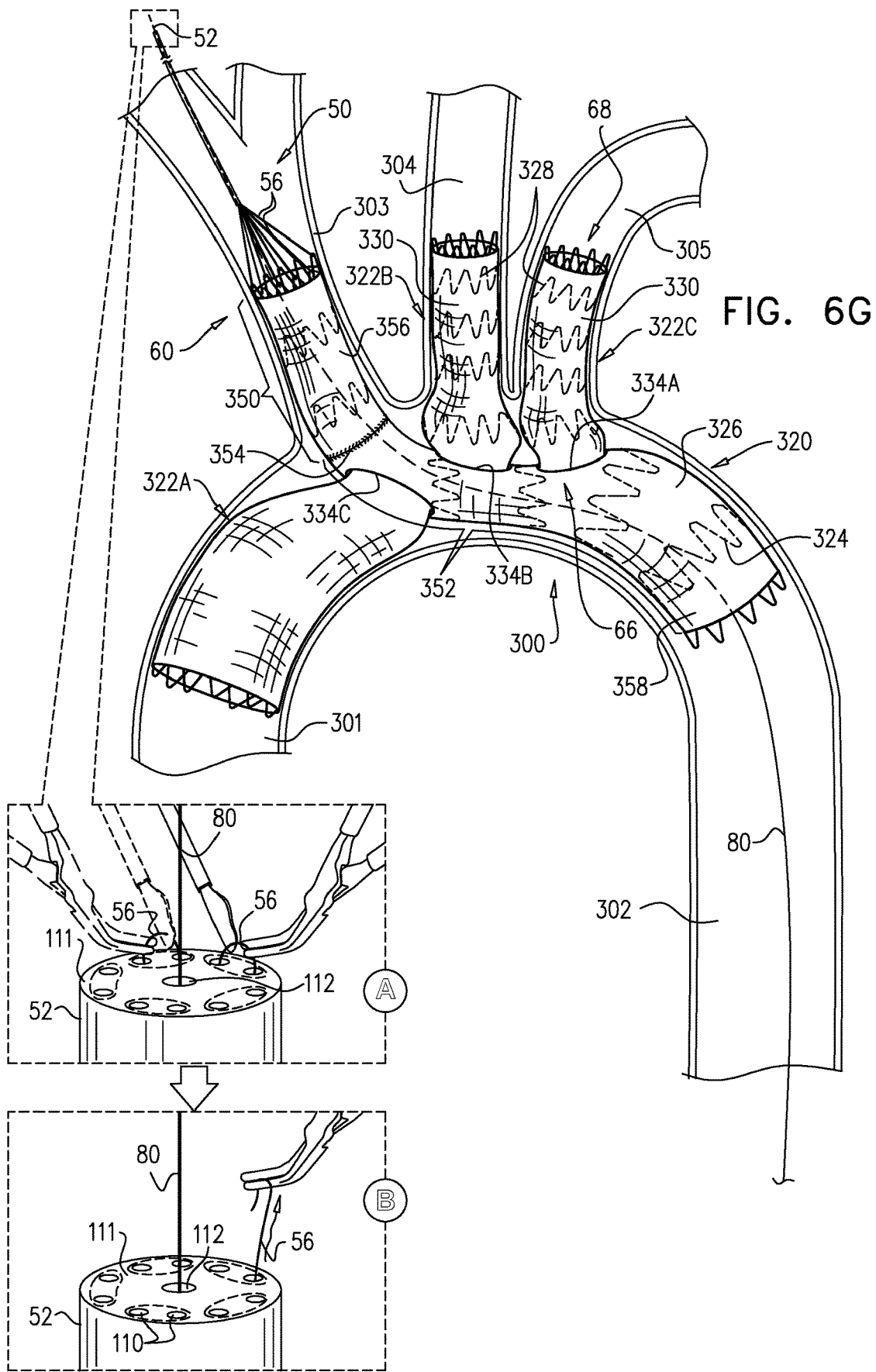

MULTI-FABRIC ENDOVASCULAR STENT-GRAFT

CROSS-REFERENCE TO RELATED APPLICATIONS

This present application is a continuation of U.S. application Ser. No. 14/759,736, filed Jul. 8, 2015, now U.S. Pat. No. 9,993,360, which is the U.S. national stage of International Application PCT/IL2014/050019, filed Jan. 7, 2014, which claims priority from U.S. Provisional Application 61/749,965, filed Jan. 8, 2013, which is assigned to the assignee of the present application and is incorporated herein by reference.

FIELD OF THE APPLICATION

This present application relates generally to prostheses and surgical methods, and specifically to tubular prostheses, including endovascular stent-grafts, and surgical techniques for using the prostheses to maintain patency of body passages such as blood vessels, and treating aneurysms and dissections of arterial walls.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs"), which may occur in one or more of the descending aorta, the ascending aorta, and the aortic arch.

Endo-Vascular Aneurysm Repair (EVAR) has transformed the practice of treatment of aortic aneurysms from an open surgical approach to a much less invasive surgical approach. The first step of an endovascular intervention usually requires introducing a delivery system into the vasculature of a patient. If the crossing profile, i.e., the external diameter, of the delivery system is 24 Fr or lower (3 Fr=1 millimeter), a true percutaneous approach may be used, because vascular closure devices are available for proper closure of such puncture sites.

SUMMARY OF THE APPLICATION

Some embodiments of the present invention provide an endovascular system, which comprises an endovascular implant and a delivery tool. The delivery tool is configured to minimize or prevent migration of the endovascular implant during an implantation procedure. The delivery tool comprises a proximal main delivery catheter, which has a distal portion in which the implant is initially disposed while in a radially-compressed delivery state. The delivery tool further comprises a distal restraining assembly, which comprises a restraining-assembly tubular shaft disposed distal to the proximal main delivery catheter. The distal restraining assembly is configured to assume (a) an engaged state, in which the distal restraining assembly prevents proximal displacement of the implant relative to the distal restraining assembly, and (b) a disengaged state, in which the distal restraining assembly does not engage the implant.

For some applications, the distal restraining assembly comprises one or more flexible elongated members, such as sutures, wires, or strings. The flexible elongated members extend from a proximal end of the restraining-assembly tubular shaft. When the distal restraining assembly is in the engaged state, the flexible elongated members releasably couple the distal restraining assembly to a distal portion of the implant.

Typically, the delivery tool further comprises a tip disposed longitudinally between the proximal main delivery catheter and the restraining-assembly tubular shaft. When the implant is in the radially-expanded deployment state and the distal restraining assembly is in the engaged state, the tip is proximally withdrawable into the implant without entangling the tip with the flexible elongated members. Typically, the flexible elongated members pass over an external surface of the tip when the distal restraining assembly is in the engaged state. The flexible elongated members are slidably disposed within the restraining-assembly tubular shaft, at least when the distal restraining assembly is in the engaged state. For some applications, the tip is conically shaped. Typically, the tip narrows toward a distal end thereof.

Typically, the endovascular system further comprises a guidewire. The delivery tool is configured to receive the guidewire therethrough, typically such that the guidewire extends from a proximal end of the proximal main delivery catheter to a distal end of the restraining-assembly tubular shaft, at least when the distal restraining assembly is in the engaged state. Typically, the proximal main delivery catheter and the restraining-assembly tubular shaft are shaped so as to define respective guidewire longitudinal lumens therethrough.

In some applications of the present invention, during a first stage of an implantation procedure, the guidewire of the delivery tool is endovascularly (preferably percutaneously) introduced into the vasculature at a first vascular access site, advanced through the vasculature, and extracted from the vasculature and the patient's body at a second vascular access site different from the first. Alternatively, the guidewire is endovascularly introduced into the vasculature at the second vascular access site, advanced through the vasculature towards the first vascular access site, captured and thereafter extracted from the vasculature and the patient's body at the first vascular access site. In either case, the guidewire extends between two vascular access sites through the vasculature. The distal restraining assembly and the proximal main delivery catheter are introduced, through the first vascular access site, into the vasculature over the guidewire. Typically, the restraining-assembly tubular shaft is advanced over the guidewire until a distal end of the restraining-assembly tubular shaft exits the vasculature through the second vascular access site, and the distal end is held (e.g., fixed and/or secured) stationary outside the patient's body. (As used in the present application, including in the claims, "fixing" or "securing" the distal end should not be understood to mean permanently fixing or securing the distal end; the distal end is in fact released later in the implantation procedure.) The restraining-assembly tubular shaft of the distal restraining assembly is positioned distal to the proximal main delivery catheter. The distal restraining assembly is in the engaged state at this stage of the implantation procedure. The tip of the delivery tool is disposed longitudinally between the proximal main delivery catheter and the restraining-assembly tubular shaft.

Respective first portions of the flexible elongated members of the distal restraining assembly extend from the proximal end of the restraining-assembly tubular shaft, and thus pass through the second vascular access site together with (within) the restraining-assembly tubular shaft, and thus are accessible from outside the patient's body. In addition, the flexible elongated members are positioned such that they pass through the restraining-assembly tubular shaft, pass over the external surface of the tip, and are releasably coupled to the distal portion of the implant.

The proximal main delivery catheter (and the distal restraining assembly) is advanced through the vasculature to a desired deployment site. The implant is released from the proximal main delivery catheter in the vasculature. The implant radially expands and transitions to the radially-expanded deployment state as it is released.

At this stage of the implantation procedure, the distal restraining assembly is still in the engaged state, in which the distal restraining assembly prevents proximal displacement of the implant relative to the distal restraining assembly. A distal end of the restraining-assembly tubular shaft is held (e.g., fixed and/or secured) stationary outside the second vascular access site, which prevents proximal movement of the restraining-assembly tubular shaft and the remainder of the distal restraining assembly, including the flexible elongated members, and thus the implant. Without using such techniques for preventing proximal movement, the implant sometimes migrates during a subsequent step of the implantation procedure, such as the advancement of one or more second implants through the implant. In addition, device motion may increase the risk of stroke.

The tip is proximally withdrawn into and through the implant. The proximal main delivery catheter is proximally withdrawn from the vasculature through the first vascular access site. At this stage of the implantation procedure, the flexible elongated members remain coupled to the distal portion of the implant. Because the flexible elongated members passed outside of the tip during the earlier stages of the procedure, the flexible elongated members do not become entangled with or otherwise interfere with the proximal withdrawal of the tip.

After the first stent-graft is released from the proximal main delivery catheter, while the distal end of the restraining-assembly tubular shaft is held (e.g., fixed and/or secured) stationary outside the second vascular access site, and before the distal restraining assembly is transitioned to the disengaged state, one or more second endovascular implants are introduced into the vasculature. The one or more second implants are advanced at least partially through the first implant, such as through a lateral opening defined by the first implant, and deployed in the vasculature. The one or more second implants are typically introduced over one or more second guidewires, separate from the guidewire over which the first implant was introduced, which typically remains in place in the vasculature during the deployment of the one or more second implants.

After deployment of the one or more second endovascular implants, the distal restraining assembly is transitioned to the disengaged state, in which the distal restraining assembly allows proximal displacement of the implant relative to the distal restraining assembly. For some applications, in order to disengage the distal restraining assembly, distal portions of the flexible elongated members that extend beyond the distal end of the restraining-assembly tubular shaft are cut, in order to release the flexible elongated members from the distal portion of the implant.

There is therefore provided, in accordance with an application of the present invention, apparatus including an endovascular system, which includes:

an endovascular implant, which is configured to assume a radially-compressed delivery state, and a radially-expanded deployment state; and
a delivery tool, which includes:
a proximal main delivery catheter, having a distal portion in which the implant is disposed while in the radially-compressed delivery state; and
a distal restraining assembly, which (a) includes a restraining-assembly tubular shaft disposed distal to the proximal main delivery catheter, and (b) which is configured to assume:
an engaged state, in which the distal restraining assembly prevents proximal displacement of the implant relative to the distal restraining assembly, and
a disengaged state, in which the distal restraining assembly allows proximal displacement of the implant relative to the distal restraining assembly.

For some applications, the distal restraining assembly includes one or more flexible elongated members, which extend from a proximal end of the restraining-assembly tubular shaft and releasably couple an element of the endovascular system to a distal portion of the implant when the distal restraining assembly is in the engaged state, the element selected from the group consisting of: the distal restraining assembly and the restraining-assembly tubular shaft. For some applications, the endovascular implant includes a stent member, and the flexible elongated members releasably couple the selected element of the endovascular system to a distal portion of the stent member when the distal restraining assembly is in the engaged state.

For some applications, the delivery tool further includes a tip disposed longitudinally between the proximal main delivery catheter and the restraining-assembly tubular shaft, and, when the implant is in the radially-expanded deployment state and the distal restraining assembly is in the engaged state, the tip is proximally withdrawable into the implant without entangling the tip with the flexible elongated members. For some applications, the flexible elongated members pass over an external surface of the tip when the distal restraining assembly is in the engaged state. For some applications, the external surface of the tip is shaped so as to define one or more grooves, and the flexible elongated members are disposed within the grooves while the flexible elongated members pass over the external surface.

For some applications, the restraining-assembly tubular shaft is shaped so as to define one or more longitudinal elongated-member lumens therethrough, through which the flexible elongated members are slidably disposed at least when the distal restraining assembly is in the engaged state. For some applications, the endovascular system further includes a guidewire, and the restraining-assembly tubular shaft is shaped so as to further define a longitudinal guidewire lumen therethrough, through which the guidewire is removably disposed. For some applications, the guidewire lumen is disposed along a central longitudinal axis of the restraining-assembly tubular shaft.

For any of the applications described above, when the endovascular implant is disposed within the proximal main delivery catheter of the delivery tool in the radially-compressed delivery state, a first longitudinal portion of the delivery tool may extend between a proximal end of the implant and a proximal end of the delivery tool, a second longitudinal portion of the delivery tool may extend between a distal end of the implant and a distal end of the delivery tool, and the first and the second longitudinal portions may have respective lengths, each of which is at least 20 cm.

For any of the applications described above, the distal restraining assembly may be configured to provide a distal disengagement site at a distal location on the restraining-assembly tubular shaft, from which site the distal restraining assembly is transitionable from the engaged state to the disengaged state.

For any of the applications described above, the delivery tool may further include a tip disposed longitudinally between the proximal main delivery catheter and the restraining-assembly tubular shaft. For some applications, the proximal main delivery catheter includes inner and outer tubular shafts, and the tip is fixed to a distal end of the inner shaft. For some applications, the tip is conically shaped. For some applications, the proximal main delivery catheter includes inner and outer tubular shafts, and the tip gradually tapers from (a) a proximal-end diameter equal to between 90% and 110% of an outer diameter of a distal end of the outer tubular shaft to (b) a distal-end diameter equal to between 70% and 100% of an outer diameter of the proximal end of the restraining-assembly tubular shaft.

For any of the applications described above, the proximal main delivery catheter may include inner and outer tubular shafts, which are longitudinally translatable with respect to each other, and the implant may be disposed radially between the inner and the outer shafts while in the radially-compressed delivery state. For some applications, the delivery tool is configured such that proximal longitudinal translation of the outer shaft relative to the inner shaft transitions the implant from the radially-compressed delivery state to the radially-expanded deployment state. For some applications, the proximal main delivery catheter includes a stopper member, which is disposed between the inner and the outer shafts, and is fixed to exactly one of the inner and the outer shafts. For some applications, the endovascular implant includes a stent member, and the stopper member is shaped and sized to interface with the stent member while the implant is in its radially-compressed delivery state, thereby substantially preventing proximal translation of the implant relative to the inner shaft as the outer shaft is proximally translated relative to the inner shaft. For some applications, the stopper member is fixed to the inner shaft. For some applications, the stopper member is positioned adjacent a distal end of the implant while the implant is in the radially-compressed delivery state, disposed radially between the inner and the outer shafts.

For any of the applications described above, the endovascular implant may include a stent-graft, which includes a flexible stent member, and a generally tubular fluid flow guide, which is securely attached to and covers at least a portion of the stent member. For some applications, the stent-graft is shaped so as to define at least one lateral opening. For some applications, the stent-graft is a first stent-graft, and the endovascular system further includes a second stent-graft, which is sized to pass at least partially through the lateral opening. For some applications, the opening is generally circular. For some applications, the stent-graft is bifurcated, and is shaped so as to define a distal main lumen, which bifurcates into two proximal branching lumens. For some applications, a length of a first one of the branching lumens is less than 90% of a length of a second one of the branching lumens. Alternatively, a length of a first one of the branching lumens is at least 10% greater than a length of a second one of the branching lumens.

For any of the applications described above, the endovascular system may further include a guidewire, and the delivery tool may be configured to receive the guidewire therethrough. For some applications, the delivery tool is configured to receive the guidewire therethrough such that the guidewire extends from a proximal end of the proximal main delivery catheter to a distal end of the restraining-assembly tubular shaft. For some applications, the proximal main delivery catheter and the restraining-assembly tubular shaft are shaped so as to define respective guidewire longitudinal lumens therethrough. For some applications, the proximal main delivery catheter includes inner and outer tubular shafts, and the inner shaft is shaped so as to define the guidewire longitudinal lumen of the proximal main delivery catheter. For some applications, the guidewire longitudinal lumen of the restraining-assembly tubular shaft is disposed along a central longitudinal axis of the restraining-assembly tubular shaft.

For any of the applications described above, the endovascular system may further include a guidewire, and the restraining-assembly tubular shaft may be shaped so as to define a longitudinal guidewire lumen therethrough, through which the guidewire is removably disposed. For some applications, the guidewire is a first guidewire, and the endovascular system includes a second guidewire.

For any of the applications described above, the endovascular implant may include a flexible stent member that includes a plurality of structural stent elements axially separate from one another.

For any of the applications described above, the distal restraining assembly may further include one or more release effector flexible elongated members, which pass from a proximal end to a distal end of the restraining-assembly tubular shaft through one or more longitudinal elongated-member lumens within the restraining-assembly tubular shaft. For some applications, the one or more release effector flexible elongated members securely engage the endovascular implant when the distal restraining assembly is in the engaged state. For some applications, the endovascular implant includes a flexible stent member, and the one or more release effector flexible elongated members securely engage the stent member when the distal restraining assembly is in the engaged state. For some applications, the endovascular implant includes a stent-graft, which includes a flexible stent member, and a generally tubular fluid flow guide, which is securely attached to and covers at least a portion of the stent member, and the release effector flexible elongated members securely engage the fluid flow guide when the distal restraining assembly is in the engaged state. For some applications, the release effector flexible elongated members are disengaged from the implant when the distal restraining assembly is in the disengaged state.

For some applications, the one or more release effector flexible elongated members pass from the distal end of the restraining-assembly tubular shaft to the proximal end of the restraining-assembly tubular shaft, engage the endovascular implant, and return to the distal end of the restraining-assembly tubular shaft, and distally extracting respective first ends of the release wires transitions the distal restraining assembly from the engaged state to the disengaged state. For some applications, the one or more release effector flexible longitudinal members are configured to transition the distal restraining assembly from the engaged state to the disengaged state by rotation of each of the flexible longitudinal members around a longitudinal axis thereof.

There is additionally provided, in accordance with an application of the present invention, apparatus including an endovascular stent-graft:
a flexible stent member; and
a tubular fluid flow guide, which includes:

a first fabric, which includes a first biologically-compatible substantially blood-impervious material, and which is attached to and covers the stent member along a first longitudinal portion of the stent-graft; and a second fabric, which includes a second biologically-compatible substantially blood-impervious material different from the first material, and which is attached to and covers the stent member along a second longitudinal portion of the stent-graft, which second longitudinal portion is at least partially non-longitudinally-overlapping with the first longitudinal portion.

For some applications, the first material is less thrombogenic than the second material. For some applications, the second material is less deformable than the first material.

For some applications:

the stent-graft is configured to assume a radially-compressed delivery state and a radially-expanded deployment state, the stent-graft has first and second ends, a perimeter of the stent-graft at the first end is less than a perimeter of the stent-graft at the second end, when the stent-graft is in the radially-expanded deployment state, and the first longitudinal portion extends to the first end of the stent-graft.

For some applications:

the stent-graft is a fenestrated stent-graft, the apparatus further includes a main stent-graft, which is shaped so as to define a lateral opening, and the second longitudinal portion of the fenestrated stent-graft is shaped so as to define an interface portion configured to form a blood-tight seal with the lateral opening of the main stent-graft.

For some applications, the first material includes expanded polytetrafluoroethylene (ePTFE).

For any of the applications described above, the second material may include a polyester.

For any of the applications described above, the first and the second longitudinal portions may be non-longitudinally-overlapping. For some applications, the first and the second longitudinal portions are longitudinally adjacent each other. For some applications, the first and the second fabrics are coupled to each other at a longitudinal junction between the first and the second longitudinal portions.

For any of the applications described above, the first and the second longitudinal portions may be partially longitudinally overlapping along a longitudinally overlapping portion of the stent-graft. For some applications, the first and the second fabrics are coupled to each other at one or more locations along the longitudinally overlapping portion. For some applications, the longitudinally overlapping portion of the stent-graft has a length that is less than 5% of an overall length of the stent-graft. For some applications, the longitudinally overlapping portion of the stent-graft has a length of between 2 and 10 mm. For some applications, the longitudinally overlapping portion of the stent-graft is positioned at a location along the stent-graft that has a diameter that is less than a greatest diameter of the stent-graft.

There is yet additionally provided, in accordance with an inventive concept 1 of the present invention, a method comprising:

providing (a) an endovascular implant and (b) a delivery tool which includes a proximal main delivery catheter and a distal restraining assembly, which includes a restraining-assembly tubular shaft disposed distal to the proximal main delivery catheter;

endovascularly introducing the delivery tool into vasculature of a patient through a first vascular access site, while the endovascular implant is disposed in a radially-compressed delivery state within a distal portion of the proximal main delivery catheter, and while the distal restraining assembly is in an engaged state with the endovascular implant, in which state the distal restraining assembly prevents proximal movement of the implant relative to the distal restraining assembly;

advancing the delivery tool through the vasculature until a distal end of the restraining-assembly tubular shaft exits the vasculature and a body of the patient through a second vascular access site;

releasing the endovascular implant from the proximal main delivery catheter, such that the endovascular implant transitions to a radially-expanded deployment state in the vasculature;

thereafter, transitioning the distal restraining assembly to a disengaged state, in which state the distal restraining assembly does not engage the implant; and thereafter, extracting the distal restraining assembly from the vasculature and the body of the patient through the second vascular access site.

Inventive concept 2. The method according to inventive concept 1, wherein endovascularly introducing and advancing the delivery tool comprise:

endovascularly introducing a guidewire of the delivery tool through one of the first and the second vascular access sites into the vasculature;

advancing the guidewire through the vasculature to the other of the first and the second vascular access sites;

extracting a portion of the guidewire from the vasculature and the body of the patient through the other of the first and the second vascular access sites, such that the guidewire extends between the first and the second vascular access sites through the vasculature; and endovascularly introducing and advancing the delivery tool over the guidewire until the distal end of the restraining-assembly tubular shaft exits the vasculature and the body of the patient through the second vascular access site.

Inventive concept 3. The method according to inventive concept 2, wherein the distal restraining assembly includes one or more flexible elongated members, which extend from a proximal end of the restraining-assembly tubular shaft and releasably couple the distal restraining assembly to a distal portion of the implant when the distal restraining assembly is in the engaged state, wherein the restraining-assembly tubular shaft is shaped so as to define one or more longitudinal elongated-member lumens and a longitudinal guidewire lumen therethrough, and wherein endovascularly introducing the delivery tool comprises endovascularly introducing the delivery tool while the flexible elongated members are slidably disposed through the longitudinal elongated-member lumens, and the guidewire is removably disposed through the longitudinal guidewire lumen.

Inventive concept 4. The method according to inventive concept 2, further comprising, after releasing the endovascular implant from the proximal main delivery catheter, using the guidewire to help hold the implant in place in the vasculature.

Inventive concept 5. The method according to inventive concept 1, further comprising fixing the distal end of the restraining-assembly tubular shaft stationary outside the second vascular access site, such that the distal restraining assembly prevents proximal displacement of the implant relative to the distal restraining assembly.

Inventive concept 6. The method according to inventive concept 5, wherein fixing stationary comprises fixing the distal end of the restraining-assembly tubular shaft stationary before releasing the endovascular implant from the proximal main delivery catheter.

Inventive concept 7. The method according to inventive concept 5, wherein fixing stationary comprises fixing the distal end of the restraining-assembly tubular shaft stationary after releasing the endovascular implant from the proximal main delivery catheter.

Inventive concept 8. The method according to inventive concept 1, further comprising, after releasing the endovascular implant, pulling the distal end of the restraining-assembly tubular shaft distally from outside the second vascular access site, thereby distally displacing the endovascular implant.

Inventive concept 9. The method according to inventive concept 1, further comprising, after releasing the endovascular implant, rotating the distal restraining assembly from outside the second vascular access site, thereby rotating the endovascular implant.

Inventive concept 10. The method according to inventive concept 9, wherein rotating the distal restraining assembly comprises rotating the restraining-assembly tubular shaft from outside the second vascular access site.

Inventive concept 11. The method according to inventive concept 1,
    wherein the distal restraining assembly includes one or more flexible elongated members, which extend from a proximal end of the restraining-assembly tubular shaft and releasably couple the distal restraining assembly to a distal portion of the implant when the distal restraining assembly is in the engaged state, and
    wherein advancing the delivery tool through the vasculature until the distal end of the restraining-assembly tubular shaft exits the vasculature through the second vascular access site comprises passing the flexible elongated members through the second vascular access site together with the distal end of the restraining-assembly tubular shaft, such that the flexible elongated members are accessible from outside a body of the patient.

Inventive concept 12. The method according to inventive concept 11, wherein endovascularly introducing the delivery tool comprises endovascularly introducing the delivery tool while the flexible elongated members releasably couple the distal restraining assembly to a distal portion of the endovascular implant, while the distal restraining assembly is in the engaged state.

Inventive concept 13. The method according to inventive concept 11, wherein transitioning the distal restraining assembly to the disengaged state comprises cutting distal portions of the flexible elongated members that extend beyond the distal end of the restraining-assembly tubular shaft.

Inventive concept 14. The method according to inventive concept 11,
    wherein the delivery tool further includes a tip, and
    wherein endovascularly introducing the delivery tool comprises endovascularly introducing the delivery tool while the tip is disposed longitudinally between the proximal main delivery catheter and the restraining-assembly tubular shaft.

Inventive concept 15. The method according to inventive concept 14, wherein releasing the endovascular implant from the proximal main delivery catheter further comprises, after the implant transitions to the radially-expanded deployment state, proximally withdrawing the tip into the implant without entangling the tip with the flexible elongated members.

Inventive concept 16. The method according to inventive concept 14, wherein providing the delivery tool comprises providing the delivery tool in which the proximal main delivery catheter includes inner and outer tubular shafts, and the tip is fixed to a distal end of the inner shaft.

Inventive concept 17. The method according to inventive concept 14, wherein providing the delivery tool comprises providing the delivery tool in which the proximal main delivery catheter comprises inner and outer tubular shafts, and the tip gradually tapers from (a) a proximal-end circumference equal to between 90% and 110% of an outer circumference of a distal end of the outer tubular shaft to (b) a distal-end circumference equal to between 70% and 100% of an outer circumference of the proximal end of the restraining-assembly tubular shaft.

Inventive concept 18. The method according to inventive concept 14, wherein endovascularly introducing the delivery tool comprises endovascularly introducing the delivery tool while the flexible elongated members pass over an external surface of the tip, while the distal restraining assembly is in the engaged state.

Inventive concept 19. The method according to inventive concept 14, wherein the external surface of the tip is shaped so as to define one or more grooves, and wherein endovascularly introducing the delivery tool comprises endovascularly introducing the delivery tool while the flexible elongated members are disposed within the grooves while the flexible elongated members pass over the external surface.

Inventive concept 20. The method according to inventive concept 1, wherein transitioning the distal restraining assembly to the disengaged state comprises transitioning the distal restraining assembly to the disengaged state from a distal disengagement site provided by the distal restraining assembly at a distal location on the restraining-assembly tubular shaft.

Inventive concept 21. The method according to inventive concept 1, wherein providing the endovascular implant comprises providing a stent-graft, which comprises a flexible stent member, and a generally tubular fluid flow guide, which is securely attached to and covers at least a portion of the stent member.

Inventive concept 22. The method according to inventive concept 21,
    wherein the stent-graft is a first stent-graft shaped so as to define at least one lateral opening,
    wherein the method further comprises providing a second stent-graft, which is sized to be securely deployed partially outside and partially inside the lateral opening,
    wherein releasing the endovascular implant from the proximal main delivery catheter comprises releasing the first stent-graft from the proximal main delivery catheter, and
    wherein the method further comprises, (a) after releasing the first stent-graft from the proximal main delivery catheter, and (c) before transitioning the distal restraining assembly to the disengaged state:
        fixing the distal end of the restraining-assembly tubular shaft stationary outside the second vascular access site, such that the distal restraining assembly prevents proximal displacement of the first stent-graft relative to the distal restraining assembly; and
        introducing the second stent-graft into the vasculature in a radially compressed state, advancing the second stent-graft partially through the lateral opening of the first stent-graft, and deploying the second stent-graft partially in the vasculature external to the lateral opening and partially inside the first stent-graft.

Inventive concept 23. The method according to inventive concept 1,
wherein endovascularly introducing and advancing the delivery tool comprise:
endovascularly introducing a first guidewire of the delivery tool through one of the first and the second vascular access sites into the vasculature;
advancing the first guidewire through the vasculature to the other of the first and the second vascular access sites;
extracting a portion of the first guidewire from the vasculature and a body of the patient through the other of the first and the second vascular access sites, such that the first guidewire extends between the first and the second vascular access sites through the vasculature; and
endovascularly introducing and advancing the delivery tool over the first guidewire until the distal end of the restraining-assembly tubular shaft exits the vasculature and the body of the patient through the second vascular access site, and
wherein introducing and advancing the second stent-graft comprises introducing a second guidewire into the vasculature through the first vascular access site, and introducing and advancing the second stent-graft over the second guidewire, while the first guidewire remains in the vasculature.

Inventive concept 24. The method according to inventive concept 1, wherein introducing the delivery tool into the vasculature comprises introducing the delivery tool into an artery.

Inventive concept 25. The method according to inventive concept 24, wherein the artery is aneurysmatic.

Inventive concept 26. The method according to inventive concept 24, wherein a wall of the artery suffers from a dissection.

There is also provided, in accordance with an inventive concept 27 of the present invention, a method comprising:
providing (a) an elongated delivery tool having proximal and distal ends, and (b) an endovascular implant, which is removably connected to the distal end of the delivery tool, such that proximal movement of the implant toward the first proximal of the delivery tool is substantially prevented;
while the endovascular implant is disposed in a radially-compressed delivery state within the delivery tool, endovascularly introducing the delivery tool into vasculature of a patient, such that (a) a proximal longitudinal portion of the delivery tool, which includes the proximal end, passes through a first vascular access site, (b) a distal longitudinal portion of the delivery tool, which includes the distal end, passes through a second vascular access site, and (c) an intermediate longitudinal portion of the delivery tool is disposed between the first and the second vascular access sites within the vasculature,
securing the distal end of the delivery tool from being substantially withdrawn into the second vascular access site;
releasing the endovascular implant from the delivery tool, such that the endovascular implant transitions to a radially-expanded deployment state in the vasculature;
removing a portion of the delivery tool from the vasculature by pulling the proximal end of delivery tool out of the first vascular access site;
effecting detachment of the distal end of the delivery tool from the implant; and
thereafter, extracting a remainder of the delivery tool from the vasculature by pulling the distal end of the delivery tool out of the second vascular access site.

Inventive concept 28. The method according to inventive concept 27, wherein releasing comprises releasing the implant from the delivery tool by longitudinally translating a component of the delivery tool toward the proximal end of the delivery tool.

Inventive concept 29. The method according to inventive concept 27, wherein endovascularly introducing comprises endovascularly introducing the delivery tool such that the implant generally spans a lesion within the blood vessel.

Inventive concept 30. The method according to inventive concept 27, wherein endovascularly introducing and advancing the delivery tool comprise:
endovascularly introducing a guidewire of the delivery tool through one of the first and the second vascular access sites into the vasculature;
advancing the guidewire through the vasculature to the other of the first and the second vascular access sites;
extracting a portion of the guidewire from the vasculature and the body of the patient through the other of the first and the second vascular access sites, such that the guidewire extends between the first and the second vascular access sites through the vasculature; and
endovascularly introducing the delivery tool over the guidewire until the distal end of the delivery tool exits the vasculature and the body of the patient through the second vascular access site.

Inventive concept 31. The method according to inventive concept 27, wherein providing the endovascular implant comprises providing a stent-graft, which comprises a flexible stent member, and a generally tubular fluid flow guide, which is securely attached to and covers at least a portion of the stent member.

Inventive concept 32. The method according to inventive concept 31,
wherein the stent-graft is a first stent-graft shaped so as to define at least one lateral opening,
wherein the method further comprises providing a second stent-graft, which is sized to pass at least partially through the lateral opening,
wherein releasing the endovascular implant from the delivery tool comprises releasing the first stent-graft from the delivery tool, and
wherein the method further comprises, (a) after releasing the first stent-graft from the delivery tool, and (c) before effecting the detachment of the distal end of the delivery tool from the first stent-graft:
fixing the distal end of the delivery tool stationary outside the second vascular access site, such that the delivery tool prevents proximal displacement of the first stent-graft relative to the distal restraining assembly; and
introducing the second stent-graft into the vasculature, advancing the second stent-graft through the lateral opening of the first stent-graft, and deploying the second stent-graft in the vasculature.

Inventive concept 33. The method according to inventive concept 32,
wherein endovascularly introducing the delivery tool comprises:
endovascularly introducing a first guidewire of the delivery tool through one of the first and the second vascular access sites into the vasculature;
advancing the first guidewire through the vasculature to the other of the first and the second vascular access sites;

extracting a portion of the first guidewire from the vasculature and the body of the patient through the other of the first and the second vascular access sites, such that the first guidewire extends between the first and the second vascular access sites through the vasculature; and endovascularly introducing the delivery tool over the first guidewire until the distal end of the delivery tool exits the vasculature and the body of the patient through the second vascular access site, and wherein introducing and advancing the second stent-graft comprises introducing a second guidewire into the vasculature through the first vascular access site, and introducing and advancing the second stent-graft over the second guidewire, while the first guidewire remains in the vasculature.

There is further provided, in accordance with an inventive concept 34 of the present invention, a method comprising:

providing an endovascular stent-graft, which includes (a) a flexible stent member, and (b) a tubular fluid flow guide, which includes (i) a first fabric, which comprises a first biologically-compatible substantially blood-impervious material, and which is attached to and covers the stent member along a first longitudinal portion of the stent-graft, and (ii) a second fabric, which comprises a second biologically-compatible substantially blood-impervious material different from the first material, and which is attached to and covers the stent member along a second longitudinal portion of the stent-graft, which second longitudinal portion is at least partially non-longitudinally-overlapping with the first longitudinal portion; and implanting the stent-graft in vasculature of a patient.

Inventive concept 35. The method according to inventive concept 34, wherein providing the stent-graft comprises providing the stent-graft in which the first material is less thrombogenic than the second material.

Inventive concept 36. The method according to inventive concept 35, wherein providing the stent-graft comprises providing the stent-graft in which the second material is stronger than the first material.

Inventive concept 37. The method according to any one of inventive concepts 35 and 36, wherein implanting the stent-graft comprises endovascularly introducing the stent-graft into the vasculature while the stent-graft is in radially-compressed delivery state, and transitioning the stent-graft to a radially-expanded deployment state in the vasculature, and wherein providing the stent-graft comprises providing the stent-graft in which a perimeter of the stent-graft at a first end thereof is less than a perimeter of the stent-graft at a second end thereof, when the stent-graft is in the radially-expanded deployment state, and the first longitudinal portion extends to the first end of the stent-graft.

Inventive concept 38. The method according to inventive concept 34, wherein implanting the stent-graft comprises positioning the stent-graft such that the second longitudinal portion is at least partially positioned in a main body lumen, and the first longitudinal portion is at least partially positioned in a branching body lumen that branched from the main body lumen.

Inventive concept 39. The method according to any one of inventive concepts 35 and 36, wherein the method further comprises providing a main stent-graft, which is shaped so as to define a lateral opening, and wherein providing the stent-graft comprises providing a branching stent graft, in which the second longitudinal portion is shaped so as to define an interface portion configured to form a blood-tight seal with the lateral opening of the main stent-graft.

Inventive concept 40. The method according to inventive concept 35, wherein providing the stent-graft comprises providing the stent-graft in which the first material comprises expanded polytetrafluoroethylene (ePTFE).

Inventive concept 41. The method according to any one of inventive concepts 34, 35, 36, and 40, wherein providing the stent-graft comprises providing the stent-graft in which the second material comprises a polyester.

Inventive concept 42. The method according to inventive concept 34, wherein providing the stent-graft comprises providing the stent-graft in which the first and the second longitudinal portions are non-longitudinally-overlapping.

Inventive concept 43. The method according to inventive concept 42, wherein providing the stent-graft comprises providing the stent-graft in which the first and the second longitudinal portions are longitudinally adjacent each other.

Inventive concept 44. The method according to inventive concept 43, wherein providing the stent-graft comprises providing the stent-graft in which the first and the second fabrics are coupled to each other at a longitudinal junction between the first and the second longitudinal portions.

Inventive concept 45. The method according to inventive concept 34, wherein providing the stent-graft comprises providing the stent-graft in which the first and the second longitudinal portions are partially longitudinally overlapping along an longitudinally overlapping portion of the stent-graft.

Inventive concept 46. The method according to inventive concept 45, wherein providing the stent-graft comprises providing the stent-graft in which the first and the second fabrics are coupled to each other at one or more locations along the longitudinally overlapping portion.

The present invention will be more fully understood from the following detailed description of embodiments thereof, taken together with the drawings, in which:

BRIEF DESCRIPTION OF THE DRAWINGS

FIG. 2A is a schematic illustration of a portion of the endovascular system of FIGS. 1A-D, in accordance with an application of the present invention;

FIG. 2B is another schematic illustration of a portion of the endovascular system of FIGS. 1A-D, in accordance with an application of the present invention;

FIG. 3 is a schematic illustration of the engagement of a distal restraining assembly with an endovascular implant, in accordance with an application of the present invention;

FIG. 4 is another schematic illustration of the engagement of a distal restraining assembly with an endovascular implant, in accordance with an application of the present invention;

FIGS. 5A-K are schematic illustrations of an exemplary method of deploying endovascular implants in an aneurysmatic abdominal aorta, using a delivery tool of the endovascular system of FIGS. 1A-D, in accordance with an application of the present invention;

FIGS. 6A-G are schematic illustrations of an exemplary method of deploying endovascular implants in an aneurysmatic aortic arch, using a delivery tool of the endovascular system of FIGS. 1A-D, in accordance with an application of the present invention;

DETAILED DESCRIPTION OF APPLICATIONS

Figure 1A:
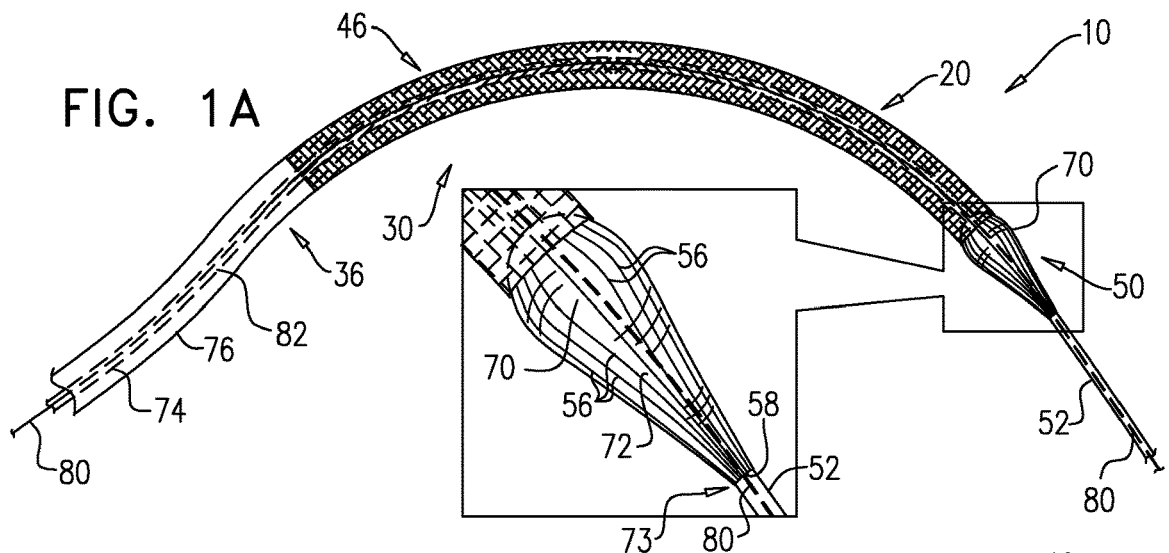
FIGS. 1A-D are schematic illustrations of several stages of deployment of an endovascular system, in accordance with an application of the present invention.
Figure 1B:
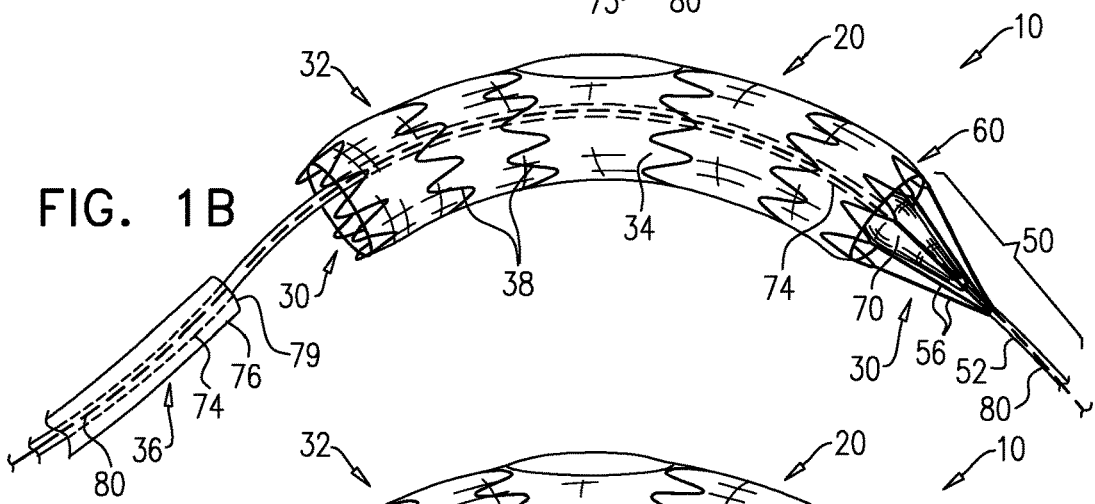
Figure 1C:
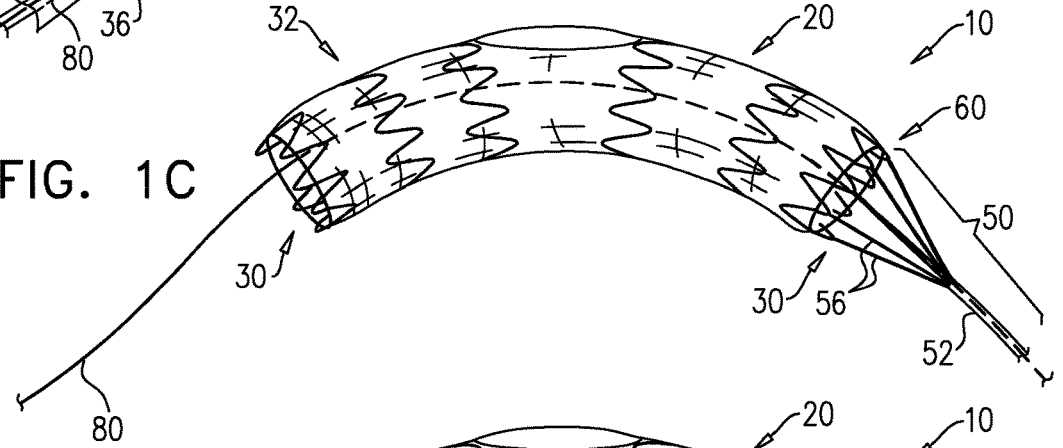
Figure 1D:
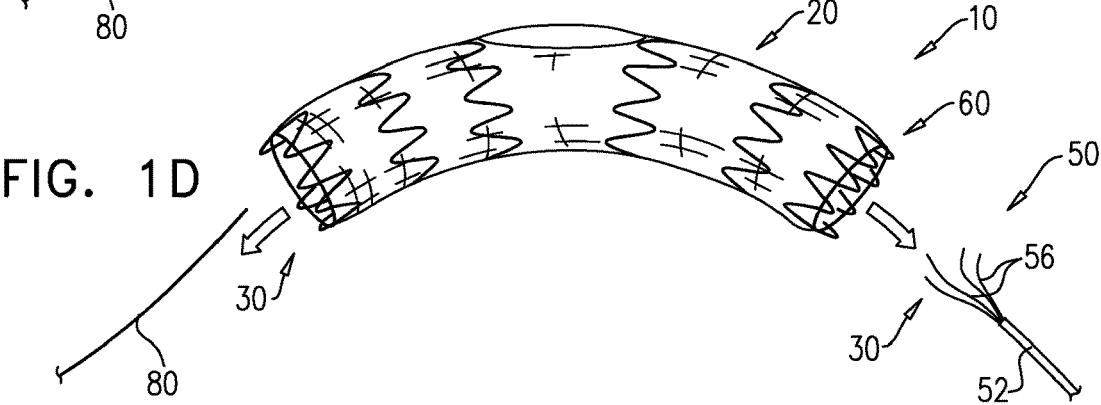

FIGS. 1A-D are schematic illustrations of several stages of deployment of an endovascular system 10, in accordance with an application of the present invention. Endovascular system 10 comprises an endovascular implant 20 and a delivery tool 30. The delivery tool is configured to minimize or prevent migration of endovascular implant 20 during an implantation procedure. Endovascular implant 20 comprises a self-expandable, typically tubular, stent member 32, and, optionally, a tubular fluid flow guide 34 (in which case endovascular implant 20 comprises a stent-graft). Endovascular implant 20 is configured to be initially positioned in a proximal main delivery catheter 36 of delivery tool 30 in a radially-compressed delivery state, such as shown in FIG. 1A, and in FIGS. 5B-C and 6B-C described hereinbelow. Endovascular implant 20 is configured to assume a radially-expanded deployment state upon being deployed from the delivery catheter in a body lumen, such as a blood vessel, such as shown in FIGS. 1B-D, and in FIGS. 5D-K and 6D-G described hereinbelow. (As used in the present application, including in the claims, "proximal" means toward the vascular access site through which the endovascular implant is introduced into the patient's vasculature, and "distal" means away from this site.)

Stent member 32 is typically flexible, and comprises a plurality of structural stent elements 38 (i.e., struts), which optionally are axially separate from one another, such as shown in FIGS. 1B-D. Fluid flow guide 34, if provided, is securely attached to structural stent elements 38, such as by suturing or stitching, such that the fluid flow guide covers at least a portion of the stent member. Structural stent elements 38 may be attached to an internal surface and/or an external surface of the fluid flow guide. Optionally, a portion of the structural stent elements may be attached (e.g., sutured) to the internal surface, and another portion to the external surface. For some applications, structural stent elements 38 comprise a metal. Alternatively or additionally, the structural stent elements comprise a self-expanding material, such that stent member 32 is self-expandable. Alternatively or additionally, the structural stent elements comprise a superelastic metal alloy, a shape memory metallic alloy, and/or Nitinol. For some applications, the stent-graft is heat-set to assume the radially-expanded state.

Fluid flow guide 34, if provided, comprises at least one piece of biologically-compatible substantially blood-impervious fabric. The fabric may comprise, for example, a polyester, a polyethylene (e.g., a poly-ethylene-terephthalate), a polymeric film material (e.g., polytetrafluoroethylene), a polymeric textile material (e.g., woven polyethylene terephthalate (PET)), natural tissue graft (e.g., saphenous vein or collagen), or a combination thereof.

Figure 5A:
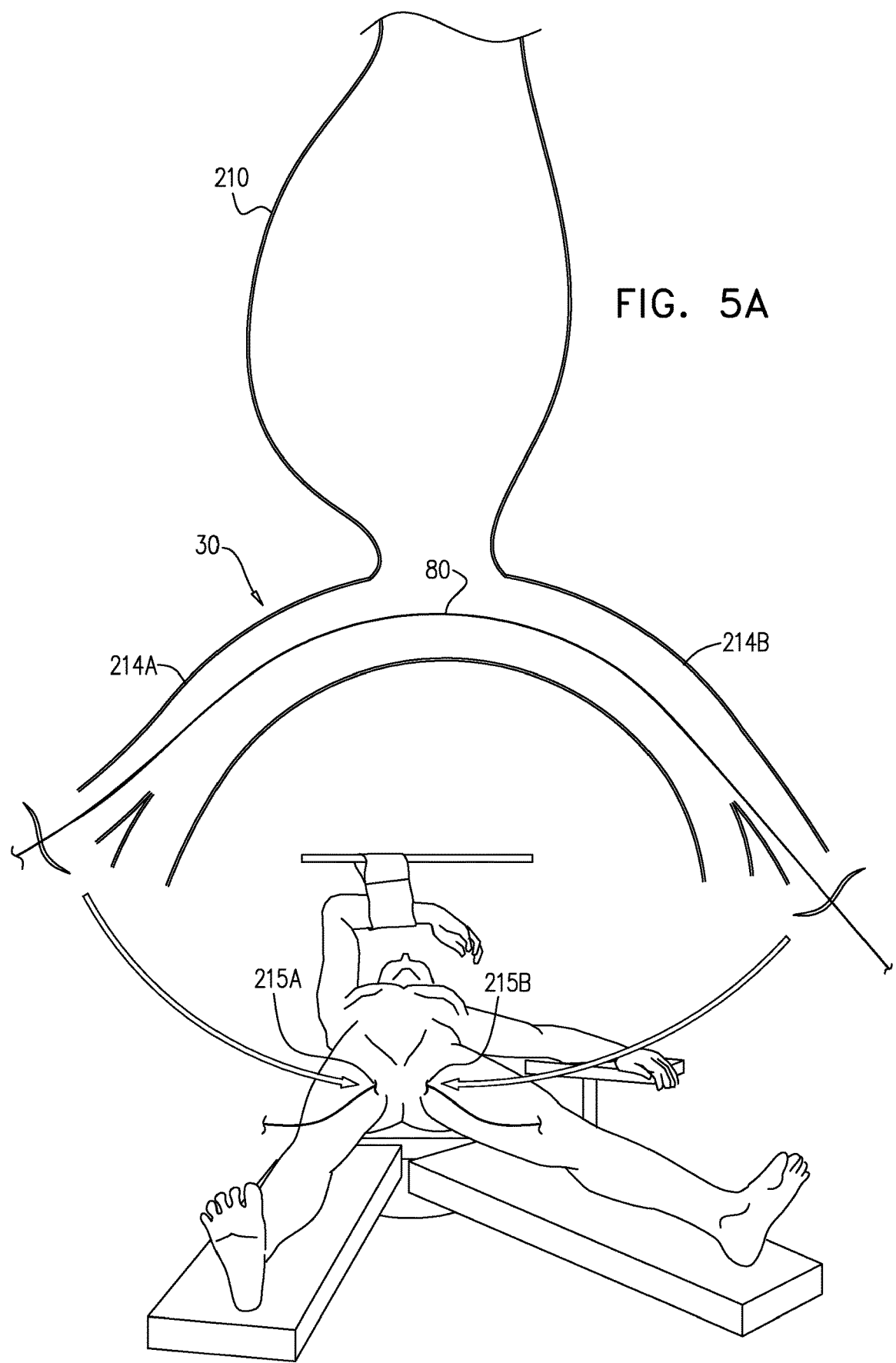
Figure 5D:
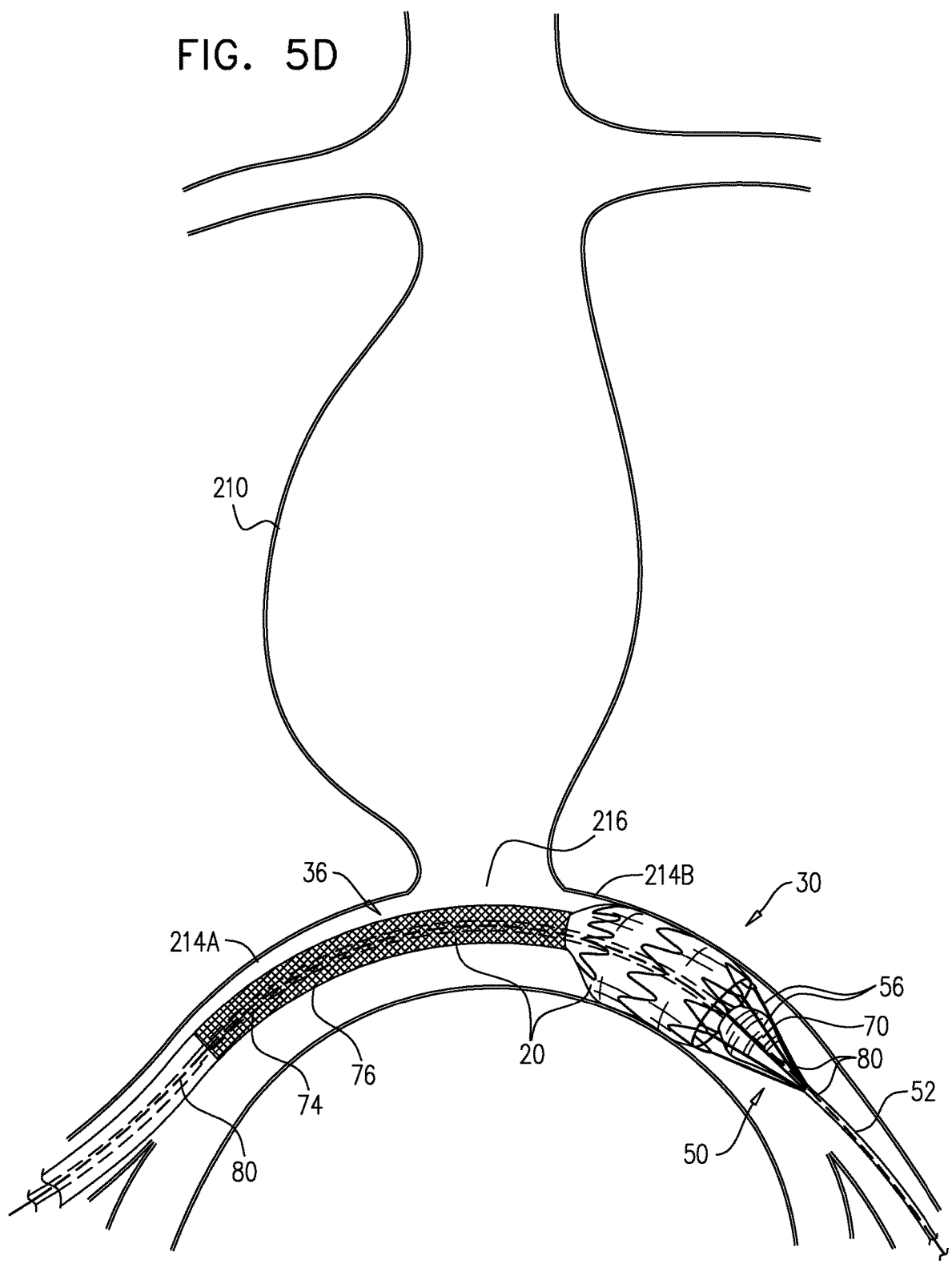
Figure 5F:
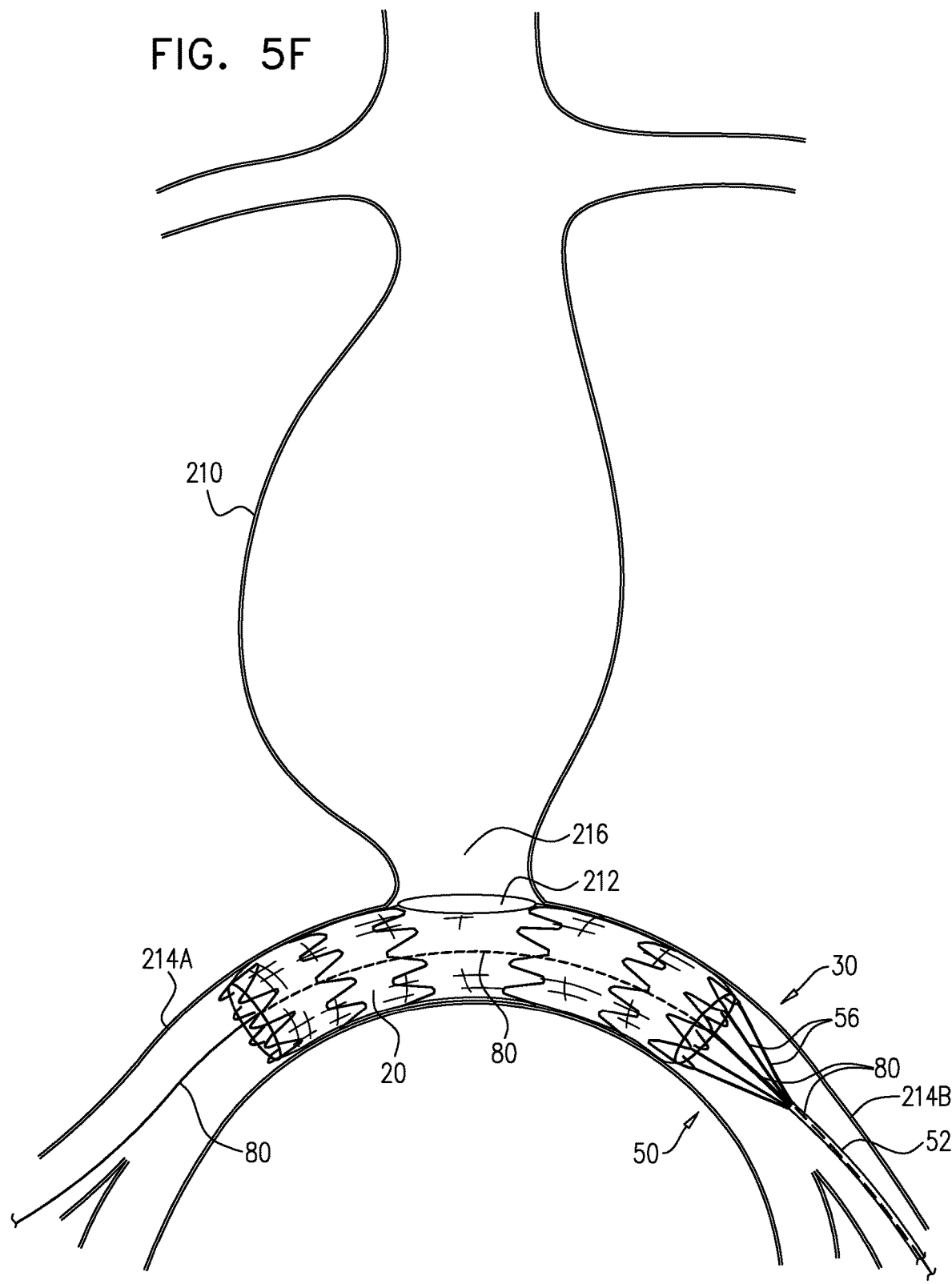
Figure 5G:
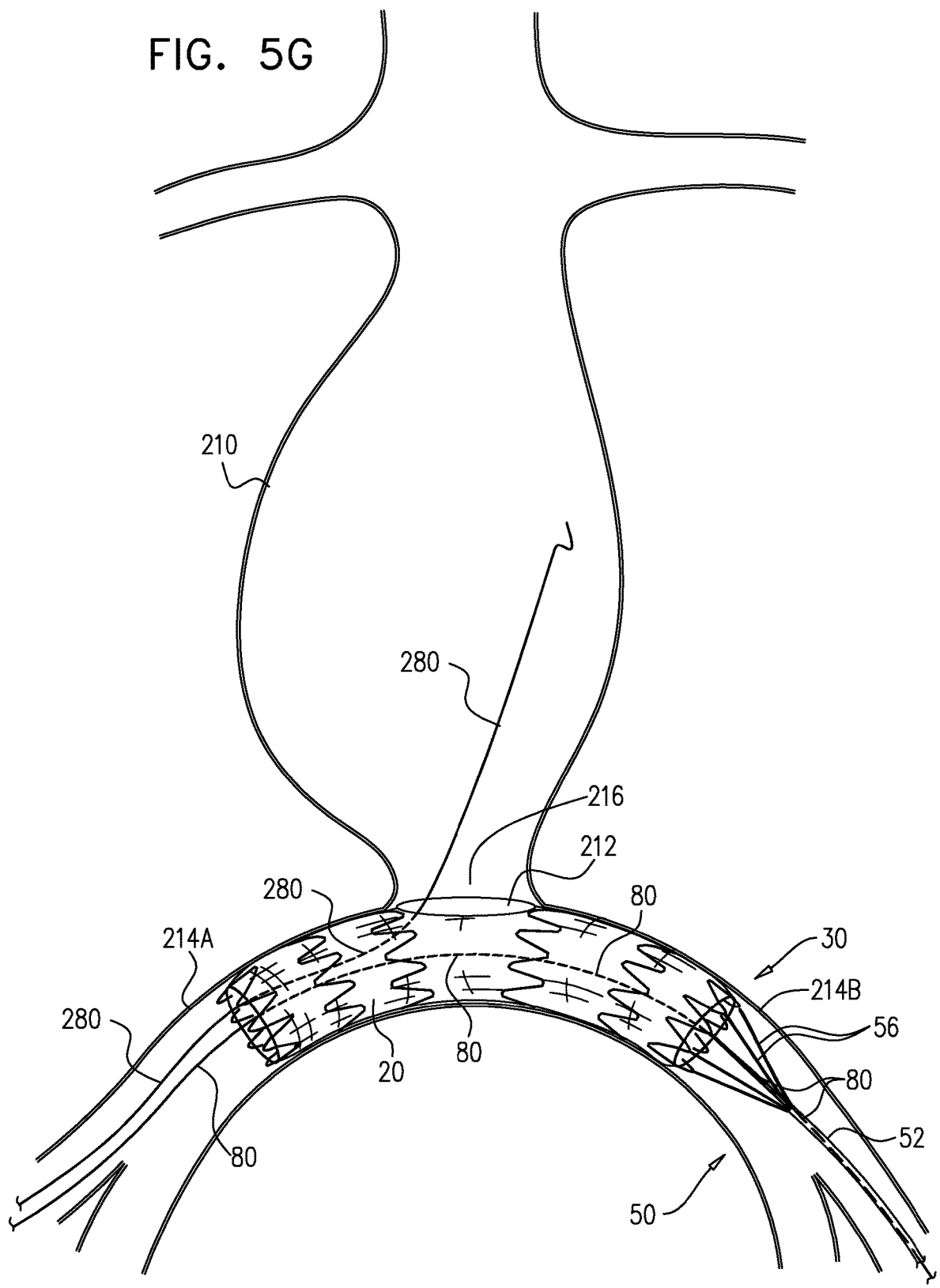
Figure 6A:
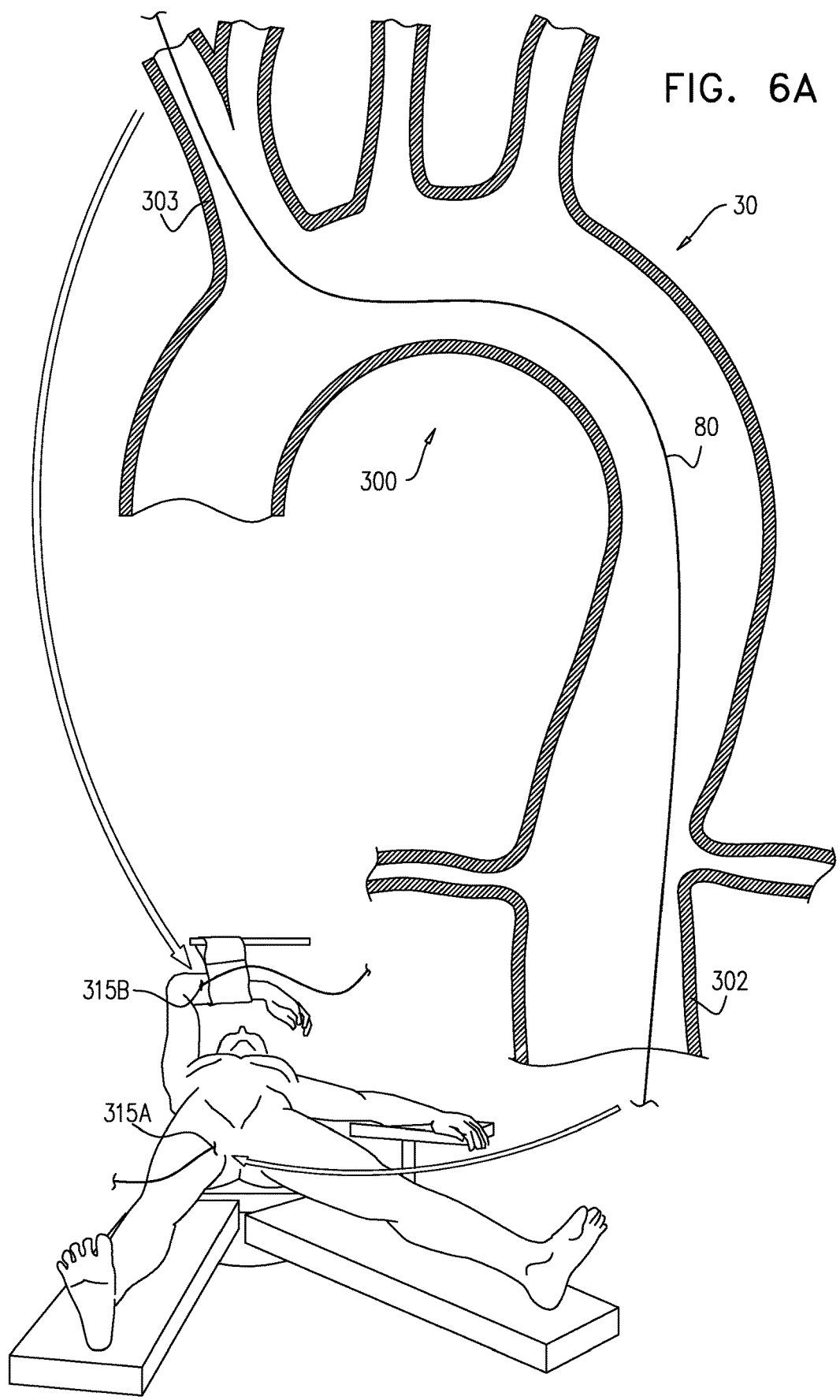
Figure 6B:
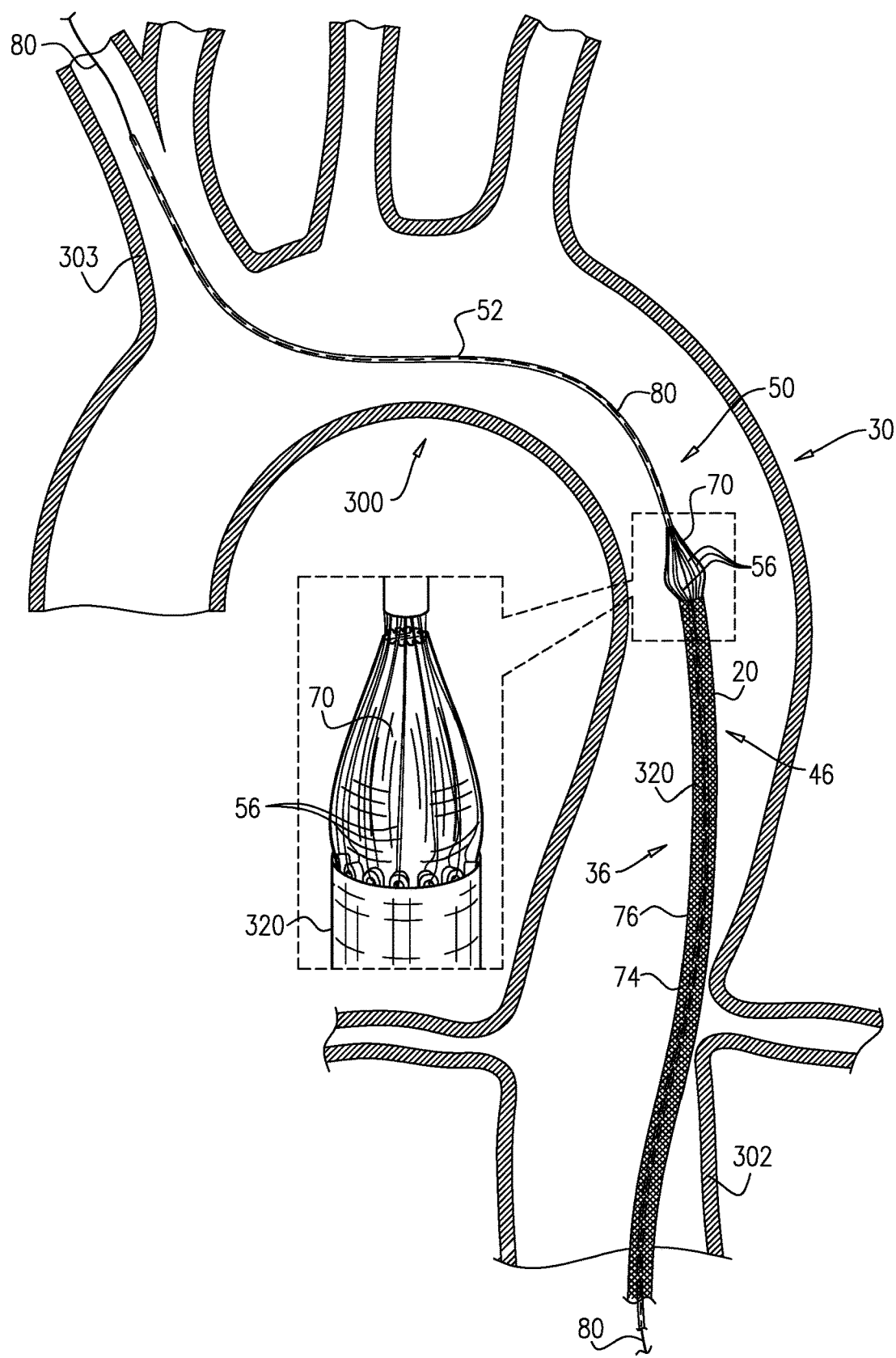
Figure 6C:
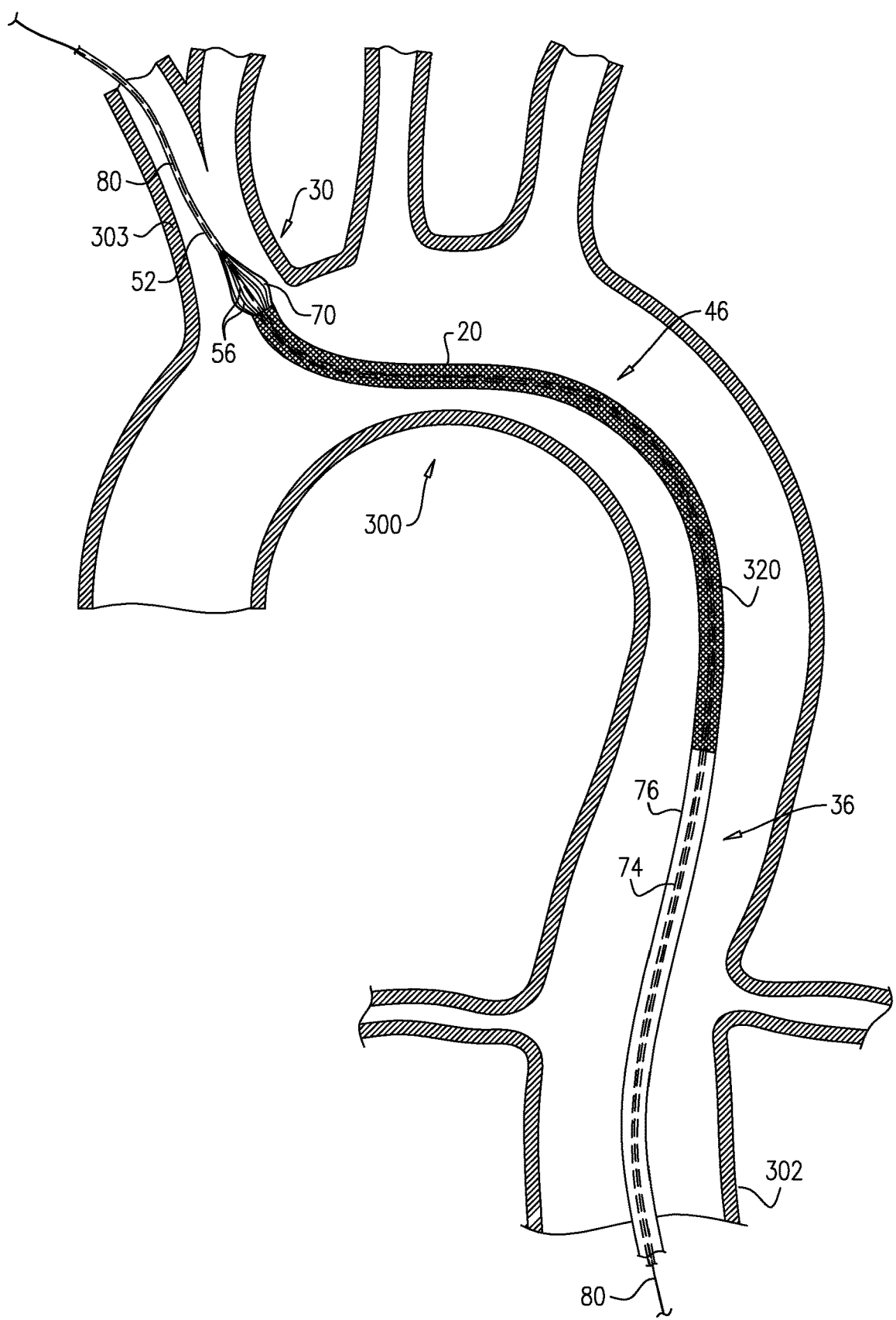
Figure 6D:
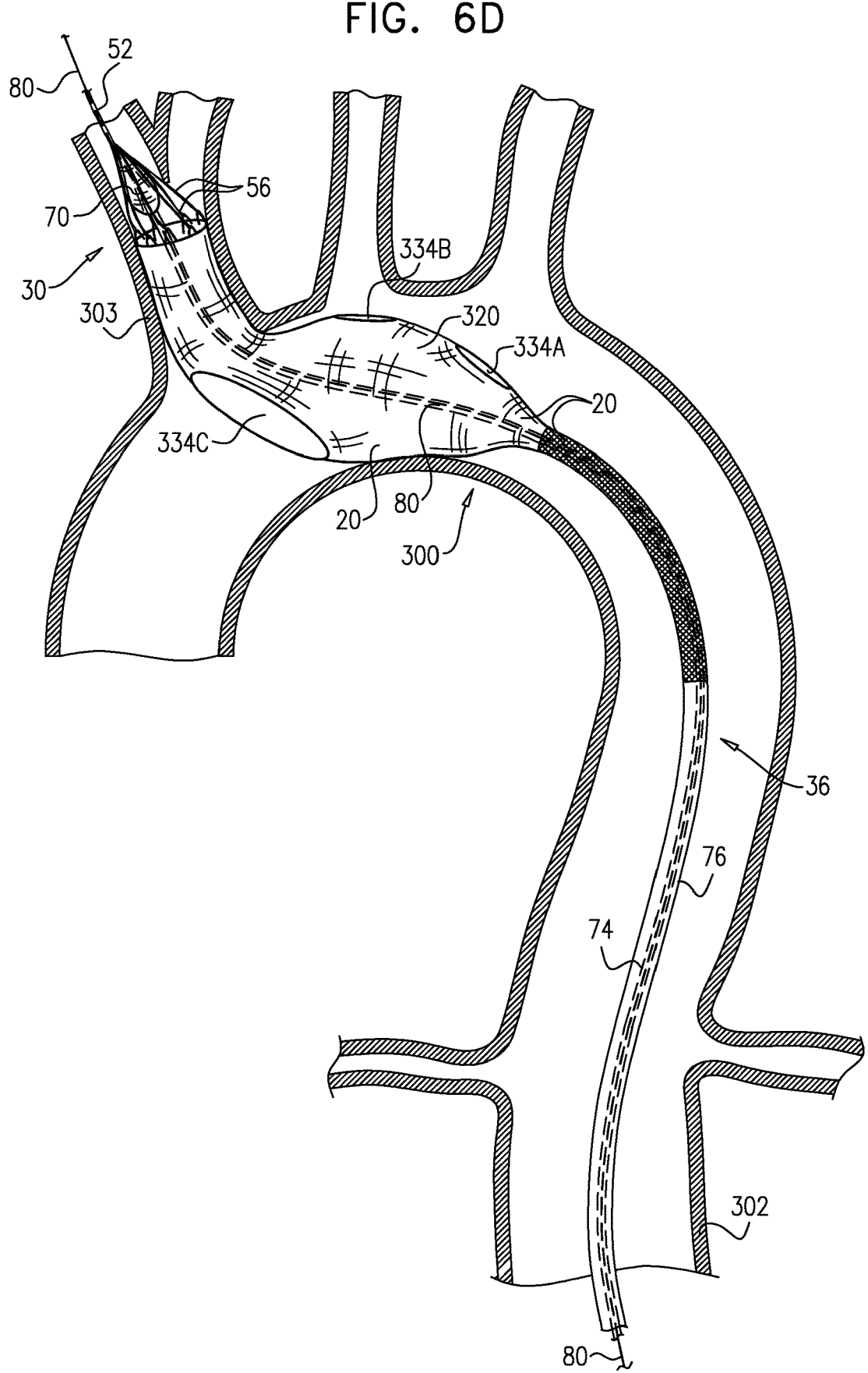
Figure 6E:
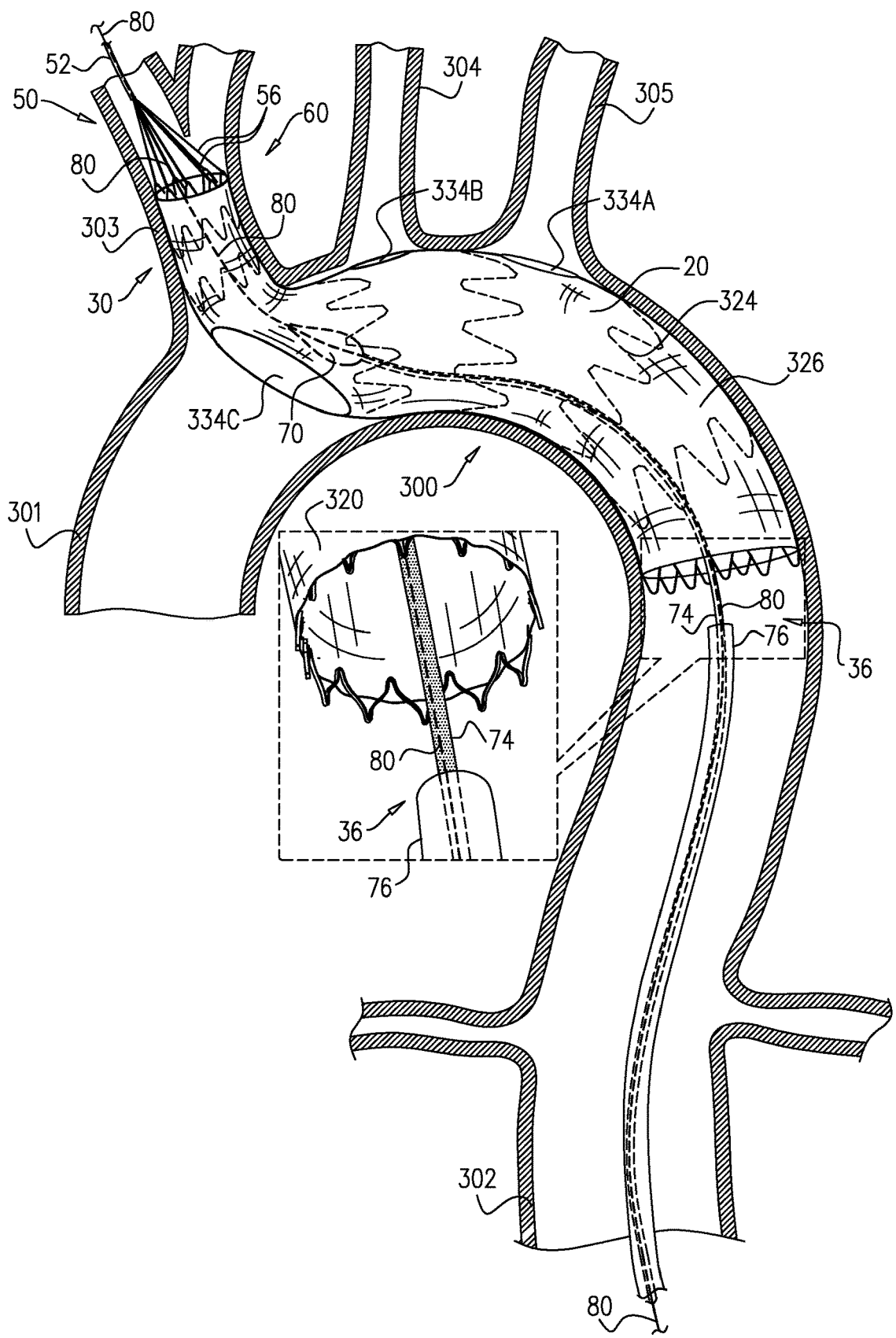
Figure 6F:
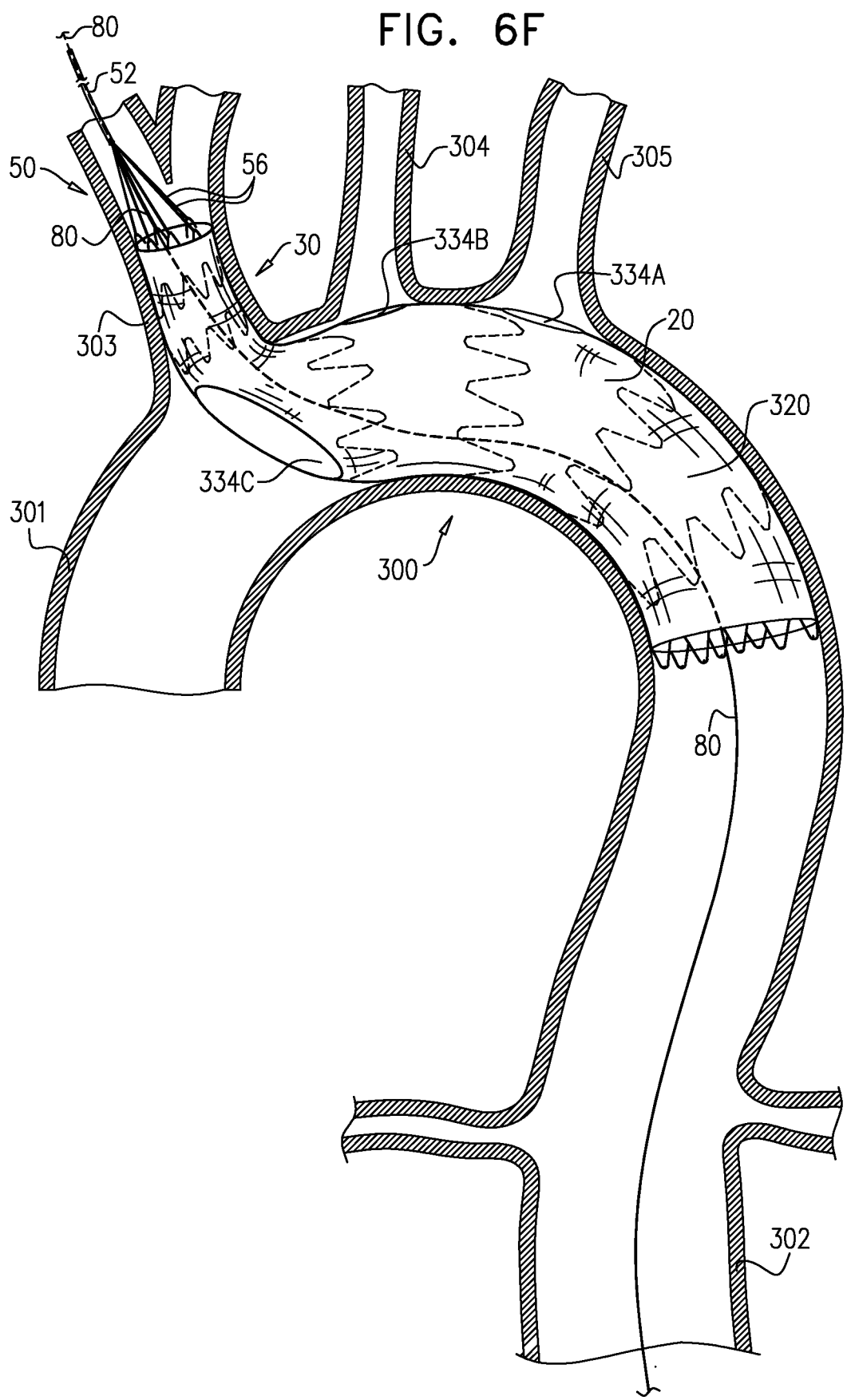

Delivery tool 30 comprises proximal main delivery catheter 36, which has a distal portion 46 in which implant 20 is disposed while in the radially-compressed delivery state, as shown in FIG. 1A (and FIGS. 5B-C and 6B-C described hereinbelow). Delivery tool 30 further comprises a distal restraining assembly 50, which comprises a restraining-assembly tubular shaft 52 disposed distal to proximal main delivery catheter 36. Distal restraining assembly 50 is configured to assume:

an engaged state, in which distal restraining assembly 50 prevents proximal displacement of implant 20 relative to distal restraining assembly 50, as shown in FIGS. 1B-C (and FIGS. 5D-J and 6D-F), and a disengaged state, in which distal restraining assembly 50 does not engage implant 20 (and FIGS. 5J and 6F).

When in the engaged state, distal restraining assembly 50 is configured to prevent distal migration of implant 20 during the implantation procedure.

Typically, restraining-assembly tubular shaft 52 has a length of between 10 and 80 cm.

For some applications, distal restraining assembly 50 comprises one or more release effector flexible elongated members 56, such as sutures, wires, or strings. Flexible elongated members 56 extend from a proximal end 58 of restraining-assembly tubular shaft 52. When distal restraining assembly 50 is in the engaged state, flexible elongated members 56 releasably couple distal restraining assembly 50 and/or restraining-assembly tubular shaft 52 to a distal portion 60 of implant 20, such as a distal portion of stent member 32 (for example, a portion of the stent member that extends distally beyond a distal end of tubular fluid flow guide 34, if provided, such as shown in FIGS. 1B-1C (and FIGS. 2A-B)), or a distal portion of tubular fluid flow guide 34, such as shown in FIG. 3. For applications in which structural stent elements 38 are axially separate from one another, flexible elongated members 56 may releasably couple distal restraining assembly 50 to distal-most one of stent element 38, or to a more proximal one of the stent elements. Typically, flexible elongated members 56 are releasably coupled to distal portion 60 of implant 20 at at least three locations on the distal portion, e.g., distributed around a circumference of the distal portion.

For some applications, when implant 20 is disposed within delivery tool 30 (typically in the proximal main delivery catheter) in the radially-compressed delivery state, a first longitudinal portion of delivery tool 30 extends between a proximal end of the implant and a first (proximal) end of the delivery tool, and a second longitudinal portion of delivery tool 30 extends between a distal end of the implant and second (distal) end of the delivery tool. The first and the second longitudinal portions have respective lengths, each of which is at least 10 cm, such as at least 20 cm. For some applications, a total length of the delivery tool is at least 60 cm.

Typically, delivery tool 30 further comprises a tip 70 disposed longitudinally between proximal main delivery catheter 36 and restraining-assembly tubular shaft 52, at least prior to deployment of implant 20 from proximal main delivery catheter 36. When implant 20 is in the radially-expanded deployment state and distal restraining assembly 50 is in the engaged state, such as shown in FIG. 1B, tip 70 is proximally withdrawable into the implant without entangling the tip with flexible elongated members 56. Typically, flexible elongated members 56 pass over an external surface 72 of tip 70 when distal restraining assembly 50 is in the engaged state. Flexible elongated members 56 are slidably disposed within restraining-assembly tubular shaft 52, at least when distal restraining assembly 50 is in the engaged state, as described in more detail hereinbelow with reference to FIGS. 2A-4. For some applications, tip 70 is conically shaped. Typically, the tip narrows toward a distal end 73 thereof.

For some applications, proximal main delivery catheter 36 comprises inner and outer tubular shafts 74 and 76. The shafts are longitudinally translatable with respect to each other, and implant 20 is disposed radially between inner and outer shafts 74 and 76 while in the radially-compressed delivery state, such as shown in FIG. 1A. Delivery tool 30 is typically configured such that proximal longitudinal translation of outer shaft 76 relative to inner shaft 74 transitions implant 20 from the radially-compressed delivery state, such as shown in FIG. 1A, to the radially-expanded deployment state, such as shown in FIG. 1B.

For some applications, tip 70 is fixed to a distal end of inner shaft 74. For some applications, tip 70 gradually tapers from (a) a proximal-end diameter $D_P$ at a proximal end 78 thereof equal to between 90% and 110% of an outer diameter $D_T$ of a distal end 79 of outer tubular shaft 76 to (b) a distal-end diameter $D_D$ at distal end 73 thereof equal to between 70% and 100% of an outer diameter $D_S$ of proximal end 58 of restraining-assembly tubular shaft 52.

Typically, endovascular system 10 further comprises a guidewire 80. Delivery tool 30 is configured to receive the guidewire therethrough, such that the delivery tool radially surrounds the guidewire. The delivery tool is advanceable over the guidewire. Typically, the delivery tool is configured to receive the guidewire therethrough such that the guidewire extends from a proximal end of proximal main delivery catheter 36 to a distal end 111 of restraining-assembly tubular shaft 52, at least when distal restraining assembly 50 is in the engaged state, as described in more detail hereinbelow with reference to FIGS. 2A-4.

Typically, proximal main delivery catheter 36 and restraining-assembly tubular shaft 52 are shaped so as to define respective guidewire longitudinal lumens 82 and 112 therethrough. For some applications, inner shaft 74 of proximal main delivery catheter 36 is shaped so as to define guidewire longitudinal lumen 82. For some applications, tip 70 is shaped so as to define a tip guidewire longitudinal lumen 84.

Reference is now made to FIG. 2A, which is a schematic illustration of a portion of endovascular system 10, in accordance with an application of the present invention. (It is noted that Section A-A and B-B are drawn to different scales.) In the configuration shown in FIG. 2A, external surface 72 of tip 70 is shaped so as to define one or more grooves 100, which generally extend longitudinally between proximal and distal ends 78 and 73 of tip 70. Flexible elongated members 56 are disposed within grooves 100 while the flexible elongated members pass over external surface 72. (It is noted that a portion of external surface 72 is within grooves 100.)

For some applications, the restraining-assembly tubular shaft 52 is shaped so as to define one or more longitudinal elongated-member lumens 110 therethrough, through which flexible elongated members 56 are slidably disposed at least when distal restraining assembly 50 is in the engaged state. Flexible elongated members 56 exit lumens 110 at distal end 111 of restraining-assembly tubular shaft 52. For some applications, flexible elongated members 56 are looped through respective sites of distal portion 60 of implant 20, and looped at distal portions of the members that extend distally out of lumens 110. Each member may be doubled, such that a first portion of the member is in one of lumens 110 and a second portion of the member is another of lumens 110. Cutting the loops of the distal portions of the members that extend out of lumens 110 frees the members from implant 20, such as described hereinbelow with reference to FIG. 5J. In this configuration, flexible elongated members 56 pass from distal end 111 of restraining-assembly tubular shaft 52 to proximal end 58 of restraining-assembly tubular shaft 52, engage the endovascular implant, and return to distal end 111.

As described above, restraining-assembly tubular shaft 52 is typically shaped so as to further define longitudinal guidewire lumen 112 therethrough, through which guidewire 80 is removably disposed. Guidewire 80 exits lumen 112 at distal end 111 of restraining-assembly tubular shaft 52. For some applications, guidewire lumen 112 is disposed along a central longitudinal axis of restraining-assembly tubular shaft 52.

Reference is now made to FIG. 2B, which is a schematic illustration of a portion of endovascular system 10, in accordance with an application of the present invention. In this configuration, proximal main delivery catheter 36 comprises a stopper member 120, which is disposed between inner and outer shafts 74 and 76, and is fixed to exactly one of the inner and the outer shafts (in FIG. 2B, it is shown fixed to inner shaft 74). Typically, the stopper member is shaped and sized to interface with structural stent elements 38 of stent member 32 while implant 20 is in its radially-compressed delivery state, thereby substantially preventing proximal translation of implant 20 relative to inner shaft 74 as outer shaft 76 is proximally translated relative to inner shaft 74. For some applications, the stopper member is fixed to inner shaft 74, as shown in FIG. 2B. After outer shaft 76 is proximally withdrawn to release the implant, stopper member 120 is proximally withdrawn through the radially-expanded implant, along with inner shaft 74 and tip 70.

For some applications, the stopper member is positioned adjacent a distal end of implant 20 while the implant is in the radially-compressed delivery state, disposed radially between inner and outer shafts 74 and 76, as shown in FIG. 2B. Typically, stopper member 120 comprises one or more engagement elements 122, which are configured to engage structural stent elements 38. For example, the engagement elements may extend is a generally distal direction, as shown in FIG. 2B.

For some applications, stopper member 120 is implemented in a delivery tool that does not comprise distal restraining assembly 50.

Reference is made to FIG. 3, which is a schematic illustration of the engagement of distal restraining assembly 50 with endovascular implant 20, in accordance with an application of the present invention. FIG. 3 shows implant 20 after the radial expansion of implant 20, as described hereinbelow with reference to FIGS. 5D and 6D, and the proximal withdrawal of tip 70, as described hereinbelow with reference to FIGS. 5E and 6E, while the distal restraining assembly is still in the engaged state.

In this configuration, flexible elongated members 56 are releasably coupled to a distal portion of tubular fluid flow guide 34. Optionally, the fluid flow guide comprises one or more eyelets, through which the elongated members pass, in order to reduce the risk of tearing the graft material of the fluid flow guide.

Reference is made to FIG. 4, which is a schematic illustration of the engagement of distal restraining assembly 50 with endovascular implant 20, in accordance with an application of the present invention. FIG. 4 shows implant 20 after the radial expansion of implant 20, as described hereinbelow with reference to FIGS. 5D and 6D, and the proximal withdrawal of tip 70, as described hereinbelow with reference to FIGS. 5E and 6E, while the distal restraining assembly is still in the engaged state.

In this configuration, flexible longitudinal members 56 are configured to transition distal restraining assembly 50 from the engaged state to the disengaged state by rotation of each of the flexible longitudinal members around a longitudinal axis thereof. For example, flexible longitudinal members 56 may be shaped so as to define proximal hooks 130. The hooks may be stiff enough to engage stent elements 38 when distal restraining assembly 50 is in the engaged state, as shown in FIG. 4, and flexible enough to straighten when withdrawn distally through longitudinal elongated-member lumens 110 of restraining-assembly tubular shaft 52 (shown in FIG. 2A).

Reference is made to FIGS. 5A-K, which are schematic illustrations of an exemplary method of deploying endovascular implant 20 and one or more second endovascular implants 200 in an aneurysmatic abdominal aorta 210, using delivery tool 30, in accordance with an application of the present invention. In this exemplary method, endovascular implant 20 and second endovascular implants 200 comprise respective stent-grafts, and endovascular implant 20 is shaped so as to define at least one lateral opening 212, such as shown in FIGS. 5E-K, which may be circular. The aortic wall may alternatively suffer from a dissection. As used in the present application, including in the claims, a "lesion" of a blood vessel means an aneurysm and/or a dissection.

As shown in FIG. 5A, during a first stage of the implantation procedure, guidewire 80 of delivery tool 30 is endovascularly (typically percutaneously) introduced into the vasculature at a first vascular access site, advanced through the vasculature, and extracted from the vasculature and the patient's body at a second vascular access site different from the first, such that the guidewire extends between two vascular access sites through the vasculature. Alternatively, guidewire 80 is introduced into the vasculature at the second vascular access site, advanced through the vasculature towards the first vascular access site, captured, and thereafter extracted from the vasculature and the patient's body at the first vascular access site. In the exemplary method illustrated in FIGS. 5A-K, the guidewire is introduced into a right iliac artery 214A through a first vascular access site 215A, such as on the right femoral artery or the right iliac artery. The guidewire is advanced across to left iliac artery 214B, and extracted from the vasculature and the patient's body through a second vascular access site 215B, such as on the left femoral artery or the left iliac artery. Alternatively, in the exemplary method illustrated in FIGS. 5A-K, the guidewire is introduced into left iliac artery 214B through second vascular access site 215B, such as on the left femoral artery or the left iliac artery. The guidewire is advanced across to right iliac artery 214A, and extracted from the vasculature and the patient's body through first vascular access site 215A, such as on the right femoral artery or the right iliac artery. (First and second vascular access sites 215A and 215B may be considered proximal and distal vascular access sites, respectively.) For example, the operator (e.g., a physician) may draw the distal end of the guidewire out through the second vascular access site using a lasso introduced to the vasculature through the exit vascular access site, or using introducer sheath introduced to the vasculature through the exit vascular access site (for example, the introducer sheath may have a diameter about equal to blood vessels as the introducer sheath narrows at the end thereof distal to the user, and the operator may radiographically introduce the guidewire into the sheath).

As shown in FIG. 5B, distal restraining assembly 50 and proximal main delivery catheter 36 are introduced, through the first vascular access site, into the vasculature over guidewire 80. Typically, restraining-assembly tubular shaft 52 is advanced over the guidewire until a distal end of the restraining-assembly tubular shaft exits the vasculature through the second vascular access site, and the distal end is held (e.g., fixed and/or secured) stationary outside the patient's body. Restraining-assembly tubular shaft 52 of distal restraining assembly 50 is positioned distal to proximal main delivery catheter 36. Distal restraining assembly 50 is in the engaged state at this stage of the implantation procedure. Tip 70 of delivery tool 30 is disposed longitudinally between proximal main delivery catheter 36 and restraining-assembly tubular shaft 52.

Respective first portions of flexible elongated members 56 of distal restraining assembly 50 extend out of distal end 111 of restraining-assembly tubular shaft 52, and thus pass through the second vascular access site together with (within) restraining-assembly tubular shaft 52, and thus are accessible from outside the patient's body. In addition, flexible elongated members 56 are positioned such that they pass through restraining-assembly tubular shaft 52 (and are typically longitudinally slidable therewithin), pass over external surface 72 of tip 70, and are releasably coupled to the distal portion of implant 20. Flexible elongated members 56 thus are configured to be effected, from a site distal to distal end 111 restraining-assembly tubular shaft 52, to effect the disengagement (i.e., release) of implant 20 from distal restraining assembly 50 at the proximal ends of the flexible elongated members.

Endovascular implant 20 is disposed radially between inner and outer shafts 74 and 76, restrained by outer shaft 76 in the radially-compressed delivery state.

As shown in FIG. 5C, proximal main delivery catheter 36 (and distal restraining assembly 50) is advanced through the vasculature to a desired deployment site. At this stage of the implantation procedure, a proximal longitudinal portion of the delivery tool, which includes a proximal end of the delivery tool, passes through first vascular access site 215A, (b) a distal longitudinal portion of the delivery tool, which includes a distal end of the delivery tool, passes through second vascular access site 215B, and (c) an intermediate longitudinal portion of the delivery tool is disposed between the first and the second vascular access sites within the vasculature.

As shown in FIG. 5D, outer shaft 76 of proximal main delivery catheter 36 is proximally withdrawn while implant 20 is held in place (optionally using distal restraining assembly 50), releasing implant 20 in the vasculature (in right and left iliac arteries 214A and 214B spanning an aorto-iliac bifurcation 216, in the illustrated method). Implant 20 radially expands and transitions to the radially-expanded deployment state as it is released. FIG. 5D shows the implant partially released from the catheter, while FIG. 5E shows the implant fully released from the catheter.

As shown in FIG. 5D (and FIGS. 5E-J), distal restraining assembly 50 is still in the engaged state, in which distal restraining assembly 50 prevents proximal displacement of implant 20 relative to distal restraining assembly 50. A distal end of restraining-assembly tubular shaft 52 is held (e.g., fixed and/or secured) stationary outside the second vascular access site, which prevents proximal movement of restraining-assembly tubular shaft 52 and the remainder of distal restraining assembly 50, including flexible elongated members 56, and thus implant 20. Without using such techniques for preventing proximal movement, the implant sometimes migrates during a subsequent step of the implantation procedure, such as the advancement of one or more second implants 200, such as described hereinbelow with reference to FIGS. 5G-K. In addition, device motion may increase the risk of stroke.

In addition, for some applications, guidewire 80 helps hold implant 20 in place in the vasculature. The operator typically fixes and/or secures (e.g., using forceps) one end (such as the distal end) of the guidewire securely outside the vasculature, while manually making a "fixed point" on the other end. Holding the guidewire tightly in place creates a more constrained path for advancement of delivery tool 30 thereover. As the delivery tool tracks over the guidewire, the delivery tool tracks a more predictable and stable trajectory inside the vasculature than if the guidewire were not secured at both ends thereof. As a result, inadvertent interaction between the delivery tool and the blood vessel wall is reduced, thereby reducing debris release and the risk of stroke. In addition, holding the guidewire tightly in place may also press one aspect of the implant against the wall of the blood vessel. This technique also helps hold the implant in place during a subsequent step of the implantation procedure, such as the advancement of one or more second implants 200, such as described hereinbelow with reference to FIGS. 5G-K. In addition, device motion may increase the risk of stroke.

These stabilization techniques allow a significantly increased level of migration resistance for the already deployed implant(s) of endovascular system 10, especially when bulky and/or stiff delivery systems containing additional branching endovascular implants of system 10 are subsequently inserted via side-facing fenestrations of a previously deployed endovascular implant, and during such deployment may exert significant longitudinal forces on the already-deployed endovascular implants.

As shown in FIG. 5E, implant 20 is fully in the radially-expanded deployment state, and tip 70 is proximally withdrawn into the implant, and the tip and inner shaft 74 of proximal main delivery catheter 36 are proximally withdrawn through the implant. Proximal main delivery catheter 36, including inner and outer shafts 74 and 76, is proximally withdrawn from the vasculature through the first vascular access site. At this stage of the implantation procedure, flexible elongated members 56 remain coupled to distal portion 60 of implant 20. Because the flexible elongated members passed outside of tip 70 during the earlier stages of the procedure, as shown in FIGS. 5B-D, the flexible elongated members do not become entangled with or otherwise interfere with the proximal withdrawal of the tip.

FIG. 5F shows implant 20 and distal restraining assembly 50 after proximal main delivery catheter 36 and tip 70 have been fully withdrawn from the patient's vasculature. In the exemplary deployment illustrated in FIG. 5F, lateral opening 212 is positioned at aorto-iliac bifurcation 216, facing aneurysmatic abdominal aorta 210. Distal restraining assembly 50 remains in the engaged state at this stage of the implantation procedure, preventing proximal movement of implant 20. Guidewire 80 may also prevent movement of implant 20, as described above with reference to FIG. 5D.

If necessary, the operator may pull the distal end of restraining-assembly tubular shaft 52 distally from outside second vascular access site 215B, thereby distally displacing endovascular implant 20. For example, such repositioning may be desired if the implant was inadvertently deployed too proximally, or if the implant slid proximally after deployment, such as during deployment of additional endovascular implants, as described immediately hereinbelow. Alternatively or additionally, if necessary the operator may rotate distal restraining assembly 50 (e.g., restraining-assembly tubular shaft 52 thereof) from outside the second vascular access site, thereby rotating endovascular implant 20. For example, such rotation may be desired the implant was inadvertently deployed with improper rotational alignment. (As mentioned above, flexible elongated members 56 may comprise wires; these wires may be configured to apply a rotational force to the implant.)

As shown in FIG. 5G-K show the subsequent deployment of two second endovascular implants 200: (a) second endovascular implant 200A in FIGS. 5G-I, and (b) second endovascular implant 200B in FIGS. 5J-K. Second endovascular implants 200 are sized to pass at least partially through lateral opening 212 of first implant 20.

As shown in FIG. 5G, a second guidewire 280 is introduced into the vasculature, typically via the first vascular access site. As mentioned above, the first guidewire 80 remains in implant 20 and the vasculature at this step of the procedure. The second guidewire is advanced into the implant through a proximal end of implant 20, and then out of the implant through lateral opening 212 and into aorta 210.

As shown in FIG. 5H, a second catheter 236, in which second endovascular implant 200A is positioned in a radially-compressed delivery state, is advanced over second guidewire 80, through a portion of the first implant 20, partially out of lateral opening 212, and into aorta 210.

As shown in FIG. 5I, second catheter 236 is proximally withdrawn, thereby deploying and transitioning second endovascular implant 200A in aorta 210, such that it is securely deployed partially outside and partially inside lateral opening 212. During the steps of the procedure described with reference to FIGS. 5G-I, distal restraining assembly 50 remains in the engaged state at this stage of the implantation procedure, preventing proximal movement of implant 20. Guidewire 80 may also prevent movement of implant 20, as described above with reference to FIG. 5D.

As shown in FIG. 5J, another second endovascular implant 200B may optionally be deployed through first implant 20 and second implant 200A, using the techniques described hereinabove with reference to FIGS. 5H-I, mutatis mutandis. Second guidewire 80, or yet another guidewire, may be used for this deployment. Typically, during the deployment of implant 200B, distal restraining assembly 50 remains in the engaged state at this stage of the implantation procedure, preventing proximal movement of implant 20. Guidewire 80 may also prevent movement of implant 20, as described above with reference to FIG. 5D.

The one or more second implants 200 are coupled to first implant 20, in order to provide one or more continuous blood-flow lumens through aneurysmatic abdominal aorta 210 to iliac arteries 214A and 214B. The implants are coupled together to form substantially blood impervious seals. As a result, blood flows through the one or more second implants 200 into first implant 20 and feeds both iliac arteries.

Also as shown in FIG. 5J, after deployment of the one or more second endovascular implants 200, distal restraining assembly 50 is transitioned to the disengaged state, in which state distal restraining assembly 50 does not engage implant 20. Disengaging distal restraining assembly 50 from implant 20 allows the distal extraction of distal restraining assembly 50 from the vasculature and the patient's body through the second vascular access site. Distal restraining assembly 50 is then removed from the patient's vasculature via the second vascular access site. It is noted that at this stage of the procedure, after the deployment of implants 200, the risk of proximal displacement of implant 20 is low even after the disengagement of distal restraining assembly 50.

For some applications, in order to disengage distal restraining assembly 50, distal portions of flexible elongated members 56 that extend beyond distal end 111 of restraining-assembly tubular shaft 52 are cut, as shown in blow-up A of FIG. 5J, in order to release the flexible elongated members from distal portion 60 of implant 20. One end of each cut member may be extracted (e.g., pulled distally) from its lumen 110, in order to disengage the member from distal portion 60 of implant 20, as shown in blow-up B of FIG. 5J. Thus, distal restraining assembly 50 is configured to provide a distal disengagement site at a distal location on restraining-assembly tubular shaft 52, from which site the distal restraining assembly is transitionable from the engaged state to the disengaged state.

FIG. 5K shows first implant 20 and one or more second implants 200 fully implanted in right and left iliac arteries 214A and 214B and aneurysmatic abdominal aorta 210, spanning aorto-iliac bifurcation 216.

Reference is made to FIGS. 6A-G, which are schematic illustrations of an exemplary method of deploying endovascular implant 20 and one or more second endovascular implants 322 in an aneurysmatic aortic arch 300, using delivery tool 30, in accordance with an application of the present invention. In this exemplary method, endovascular implant 20 comprises an endovascular stent-graft 320, which comprises a stent member 324 and a fluid flow guide 326, and second endovascular implants 322 comprise respective stent-grafts, which comprise respective stent members 328 and fluid flow guides 330. The aortic wall may alternatively suffer from a dissection.

In the particular configuration described with reference to FIGS. 6A-G, and shown in FIGS. 6D-G, stent-graft 320 is generally similar to, and may implement any or all of the features of first stent-graft 20, described with reference to FIGS. 4-6H of PCT Publication WO 2011/064782, which is incorporated herein by reference. In particular, stent-graft 320 is shaped so as to define three first lateral openings 334 through stent-graft 320 when the stent-graft is in its radially-expanded state:

a proximal superior first lateral opening 334A;
a distal superior first lateral opening 334B; and
a distal inferior first lateral opening 334C.

Typically, when stent-graft 320 is unconstrained in its radially-expanded state, proximal and distal superior first lateral openings 334A and 334B face in a first radial direction, and distal inferior first lateral opening 334C faces in a second radially direction generally circumferentially opposite the first radial direction. For example, if the stent-graft is viewed from one end, proximal and distal superior first lateral openings 334A and 334B may be disposed at between 11 o'clock and 1 o'clock (e.g., at 12 o'clock), and distal inferior first lateral opening 334C may be disposed at between 5 o'clock and 7 o'clock (e.g., at 6 o'clock).

As shown in FIG. 6A, during a first stage of the implantation procedure, guidewire 80 of delivery tool 30 is endovascularly (preferably percutaneously) introduced into the vasculature at a first vascular access site, advanced through the vasculature, and extracted from the vasculature and the patient's body at a second vascular access site different from the first, such that the guidewire extends between two vascular access sites through the vasculature. Alternatively, guidewire 80 is introduced into the vasculature at the second vascular access site, advanced through the vasculature, and extracted from the vasculature and the patient's body at the first vascular access site. In the exemplary method illustrated in FIGS. 6A-G, the guidewire is introduced into aortic arch 100 via one of the iliac arteries through a first vascular access site 315A, such as on the right femoral artery or the right iliac artery. The guidewire is advanced up a descending aorta 302 and into a first one of the branches of the aortic arch, such as a brachiocephalic artery 303, and extracted from the vasculature and the patient's body through a second vascular access site 315B, such as on the brachial artery. Alternatively, in the exemplary method illustrated in FIGS. 6A-G, the guidewire is introduced into a first one of the branches of the aortic arch, such as brachiocephalic artery 303, through second vascular access site 315B, such as on the brachial artery. The guidewire is advanced into aortic arch 100, advanced down descending aorta 302 and one of the iliac arteries, and extracted from the vasculature and the patient's body through first vascular access site 315A, such as on the right femoral artery or the right iliac artery. (First and second vascular access sites 315A and 315B may be considered proximal and distal vascular access sites, respectively.) For example, the operator may draw the distal end of the guidewire out through the exit vascular access site using a lasso introduced to the vasculature through the exit vascular access site, or using introducer sheath introduced to the vasculature through the exit vascular access site (for example, the introducer sheath may have a diameter about equal to blood vessels as the introducer sheath narrows at the end thereof distal to the user, and the operator may radiographically introduce the guidewire into the sheath).

As shown in FIG. 6B, distal restraining assembly 50 and proximal main delivery catheter 36 are introduced, through the first vascular access site, into the vasculature over guidewire 80. Typically, restraining-assembly tubular shaft 52 is advanced over the guidewire until a distal end of the restraining-assembly tubular shaft exits the vasculature through the second vascular access site, and the distal end is held (e.g., fixed and/or secured) stationary outside the patient's body. Restraining-assembly tubular shaft 52 of distal restraining assembly 50 is positioned distal to proximal main delivery catheter 36. Distal restraining assembly 50 is in the engaged state at this stage of the implantation procedure. Tip 70 of delivery tool 30 is disposed longitudinally between proximal main delivery catheter 36 and restraining-assembly tubular shaft 52. Flexible elongated members 56 of distal restraining assembly 50 pass through restraining-assembly tubular shaft 52, pass over external surface 72 of tip 70, and are releasably coupled to the distal portion of stent-graft 320. Stent-graft 320 is disposed radially between inner and outer shafts 74 and 76, restrained by outer shaft 76 in the radially-compressed delivery state.

As shown in FIG. 6C, main delivery catheter 36 is advanced over guidewire 80, until stent-graft 320 is partially disposed in brachiocephalic artery 103, partially disposed in aortic arch 100, and partially disposed an upper part of descending aorta 302. At this stage of the implantation procedure, a proximal longitudinal portion of the delivery tool, which includes a proximal end of the delivery tool, passes through first vascular access site 315A, (b) a distal longitudinal portion of the delivery tool, which includes a distal end of the delivery tool, passes through second vascular access site 315B, and (c) an intermediate longitudinal portion of the delivery tool is disposed between the first and the second vascular access sites within the vasculature.

As shown in FIG. 6D, outer shaft 76 of proximal main delivery catheter 36 is proximally withdrawn while stent-graft 320 is held in place (optionally using distal restraining assembly 50), releasing stent-graft 320 in the vasculature. Stent-graft 320 radially expands and transitions to the radially-expanded deployment state as it is released. FIG. 6D shows the implant partially released from the catheter, while FIG. 6E shows the implant fully released from the catheter.

As shown in FIG. 6D (and FIGS. 6E-F), distal restraining assembly 50 is still in the engaged state, in which distal restraining assembly 50 prevents proximal displacement of stent-graft 320 relative to distal restraining assembly 50. A distal end of restraining-assembly tubular shaft 52 is held (e.g., fixed and/or secured) stationary outside the second vascular access site, which prevents proximal movement of restraining-assembly tubular shaft 52 and the remainder of distal restraining assembly 50, including flexible elongated members 56, and thus stent-graft 320. Without using such techniques for preventing proximal movement, the implant sometimes migrates during a subsequent step of the implantation procedure, such as the advancement of one or more second endovascular stent-grafts 322, such as described hereinbelow with reference to FIG. 6G. In addition, device motion may increase the risk of stroke.

In addition, for some applications, guidewire 80 helps hold stent-graft 320 in place. The operator typically fixes and/or secures (e.g., using forceps) one end (such as the distal end) of the guidewire securely outside the vasculature, while manually making a "fixed point" on the other end. Holding the guidewire tightly in place creates a more constrained path for advancement of delivery tool 30 thereover. As the delivery tool tracks over the guidewire, the delivery tool tracks a more predictable and stable trajectory inside the vasculature than if the guidewire were not secured at both ends thereof. As a result, inadvertent interaction between the delivery tool and the blood vessel wall is reduced, thereby reducing debris release and the risk of stroke. In addition, holding the guidewire tightly in place may also press one aspect of the implant against the wall of the blood vessel. This technique also helps hold the implant in place during a subsequent step of the implantation procedure, such as the advancement of one or more second endovascular stent-grafts 322, such as described hereinbelow with reference to FIG. 6G. In addition, device motion may increase the risk of stroke.

These stabilization techniques allow a significantly increased level of migration resistance for the already deployed implant(s) of endovascular system 10, especially when bulky and/or stiff delivery systems containing additional branching endovascular implants of system 10 are subsequently inserted via side-facing fenestrations of a previously deployed endovascular implant, and during such deployment may exert significant longitudinal forces on the already-deployed endovascular implants.

As shown in FIG. 6E, stent-graft 320 is fully in the radially-expanded deployment state, and tip 70 and inner shaft 74 of proximal main delivery catheter 36 are proximally withdrawn through the implant. At this stage of the implantation procedure, flexible elongated members 56 remain coupled to distal portion 60 of stent-graft 320. Because the flexible elongated members passed outside of tip 70 during the earlier stages of the procedure, as shown in FIGS. 6B-D, the flexible elongated members do not interfere with the proximal withdrawal of the tip.

FIG. 6F shows stent-graft 320 and distal restraining assembly 50 after proximal main delivery catheter 36 and tip 70 have been fully withdrawn from the patient's vasculature. In the exemplary deployment illustrated in FIG. 6F, a proximal portion of stent-graft 320, including a proximal end thereof, is positioned in the upper part of descending aorta 302, a middle portion of stent-graft 320 is positioned in aortic arch 300, and a distal portion of stent-graft 320, including a distal end thereof, is positioned in brachiocephalic artery 303. Proximal superior first lateral opening 334A faces toward and is aligned with a left subclavian artery 305, and distal superior first lateral opening 334B faces toward and is aligned with left common carotid artery 304. Distal inferior first lateral opening 334C is disposed in aortic arch 300 facing upstream, generally toward an ascending aorta 301, in a vicinity of the bifurcation of aortic arch 300 and brachiocephalic artery 303. For some applications, proper rotational alignment and/or axial orientation of the first lateral openings are achieved using fluoroscopy. For example, stent-graft 320 may comprise one or more radiopaque markers in a vicinity (e.g., on a periphery of) the first lateral openings.

Distal restraining assembly 50 remains in the engaged state at this stage of the implantation procedure, preventing proximal movement of stent-graft 320. Guidewire 80 may also prevent movement of stent-graft 320, as described above with reference to FIG. 6D.

If necessary, the operator may pull the distal end of restraining-assembly tubular shaft 52 distally from outside second vascular access site 315B, thereby distally displacing stent-graft 320. For example, such repositioning may be desired if the stent-graft was inadvertently deployed too proximally, or if the stent-graft slid proximally after deployment, such as during deployment of additional stent-grafts, as described immediately hereinbelow. Alternatively or additionally, if necessary the operator may rotate distal restraining assembly 50 (e.g., restraining-assembly tubular shaft 52 thereof) from outside the second vascular access site, thereby rotating stent-graft 320. For example, such rotation may be desired the implant was inadvertently deployed with improper rotational alignment. (As mentioned above, flexible elongated members 56 may comprise wires; these wires may be configured to apply a rotational force to the stent-graft.)

FIG. 6G shows stent-graft 320 and distal restraining assembly 50 after the subsequent deployment of three second endovascular stent-grafts 322. Distal restraining assembly 50 remains in the engaged state, and guidewire 80 remains in place, during the deployment of these three second endovascular stent-grafts. These three second endovascular stent-grafts are deployed using one or more guidewires and delivery catheters separate from guidewire 80 and proximal main delivery catheter 36. In the illustrated deployment, these three second endovascular stent-grafts comprise:

second endovascular stent-graft 322A, which is deployed up descending aorta 302, through a proximal portion of stent-graft 320, partially out of distal inferior first lateral opening 334C, and into aortic arch 300 and/or the upper part of ascending aorta 301, such as described with reference to FIGS. 6B-D of the above-mentioned '782 publication; second endovascular stent-graft 322A is thus securely deployed partially outside and partially inside lateral opening 334C;

second endovascular stent-graft 322B, which is deployed up descending aorta 302, through a proximal portion of stent-graft 320, partially out of one of proximal superior first lateral opening 334A and distal superior first lateral opening 334B, and into a second one of the branches of aortic arch 300, such as left common carotid artery 304 or left subclavian artery 305, such as described with reference to FIGS. 6E-F of the '782 publication; second endovascular stent-graft 322B is thus securely deployed partially outside and partially inside lateral opening 334A; and third endovascular stent-graft 322C, which is deployed up descending aorta 302, through a proximal portion of stent-graft 320, partially out of the other one of proximal superior first lateral opening 334A and distal superior first lateral opening 334B, and into a second one of the branches of aortic arch 300, such as left common carotid artery 304 or left subclavian artery 305, such as described with reference to FIG. 6H of the '782 publication; second endovascular stent-graft 322C is thus securely deployed partially outside and partially inside lateral opening 334B.

As can be seen in FIG. 6G, upon deployment of all four stent-grafts, the multi-component stent-graft system defines a blood-flow path from ascending aorta 301, over aortic arch 300, and to descending aorta 302. The multi-component stent-graft system additionally provides blood-flow paths to the three branches of the aortic arch: brachiocephalic artery 303, left common carotid artery 304, and left subclavian artery 305.

Also as shown in FIG. 6G, after deployment of the one or more second endovascular stent-grafts 322, distal restraining assembly 50 is transitioned to the disengaged state, in which distal restraining assembly 50 allows proximal displacement of stent-graft 320 relative to distal restraining assembly 50. For some applications, in order to disengage distal restraining assembly 50, distal portions of flexible elongated members 56 that extend beyond distal end 111 of restraining-assembly tubular shaft 52 are cut, as shown in blow-up A of FIG. 6G, in order to release the flexible elongated members from distal portion 60 of stent-graft 320. One end of each cut member may be pulled distally from its lumen 110, in order to disengage the member from distal portion 60 of stent-graft 320, as shown in blow-up B of FIG. 6G. Thus, distal restraining assembly 50 is configured to provide a distal disengagement site at a distal location on restraining-assembly tubular shaft 52, from which site the distal restraining assembly is transitionable from the engaged state to the disengaged state. Distal restraining assembly 50 is then removed from the patient's vasculature via the second vascular access site.

Figure 7:
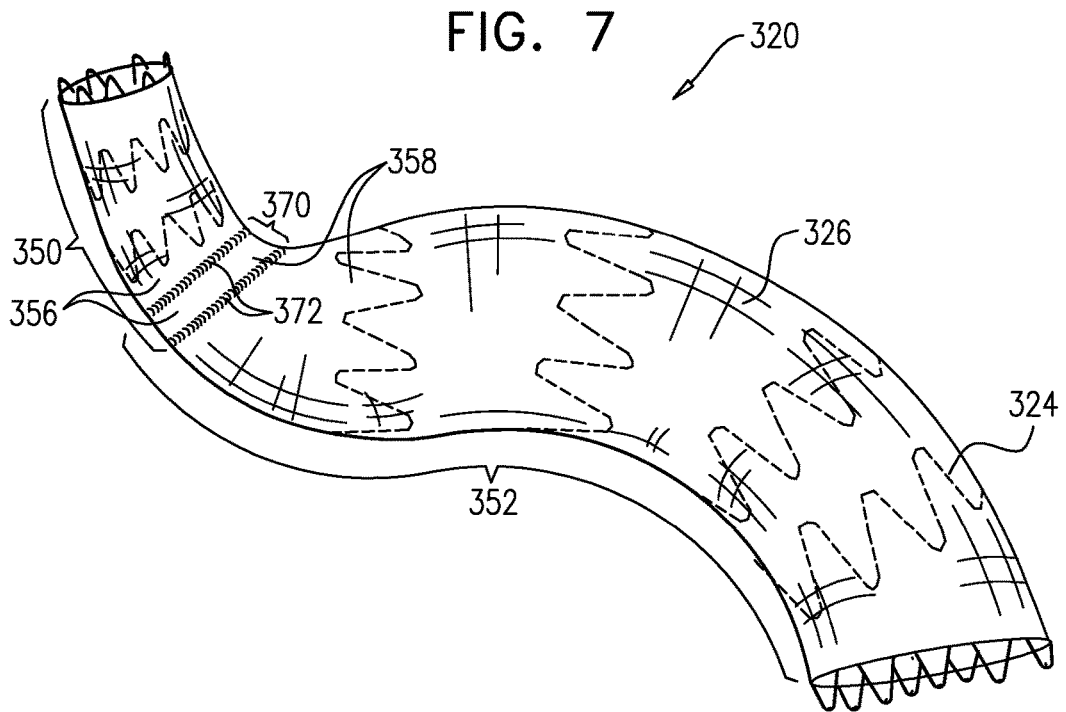
FIG. 7 is a schematic illustration of an alternative configuration of a stent-graft of FIG. 6G, in accordance with an application of the present invention.
Figure 8:
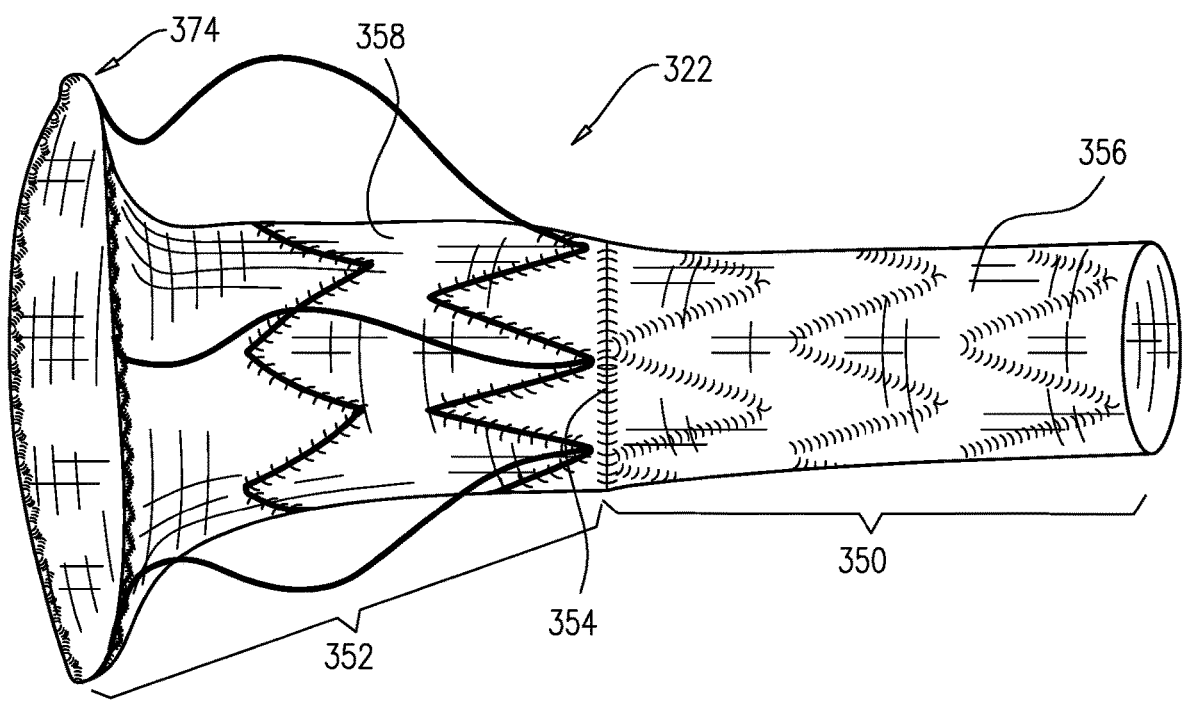
FIG. 8 is a schematic illustration of one of the second endovascular stent-grafts of FIG. 6G, in accordance with an application of the present invention.

Reference is still made to FIG. 6G, and is also made to FIG. 7, which is a schematic illustration of an alternative configuration of stent-graft 320, in accordance with an application of the present invention, and to FIG. 8, which is a schematic illustration of one of second endovascular stent-grafts 322, in accordance with an application of the present invention. For some applications, a stent-graft is provided that comprises a tubular flow guide that comprises two fabrics that comprise two different biologically-compatible substantially blood-impervious materials, such as expanded polytetrafluoroethylene (ePTFE) and polyester (e.g., polyethylene terephthalate (PET).

For some applications, endovascular stent-graft 320 comprises two different fabrics. Fluid flow guide 326 of endovascular stent-graft 320 comprises first and second fabrics 356 and 358, which are attached to and cover stent member 324 along first and second longitudinal portions 350 and 352 of stent-graft 320. First and second longitudinal portions 350 and 352 are at least partially non-longitudinally-overlapping.

First and second fabrics 356 and 358 comprise first and second biologically-compatible substantially blood-impervious materials, respectively, which are different from each other. Typically, the first material is less thrombogenic than the second material, and may comprise, for example, ePTFE. As used in the present application, including in the claims, "thrombogenic" means the tendency of a material in contact with the blood to produce a thrombus or embolus. Typically, the second material less deformable than the first material, and may comprise, for example, polyester, such as a biostable polymer, e.g., PET.

Typically, first longitudinal portion 350 is located along a narrower portion of the stent-graft that is configured to be positioned in a smaller blood vessel, such as one of the branches of the aortic arch feeding the cranial circulation. For some applications, a perimeter of stent-graft 320 at first end thereof is less than a perimeter of stent-graft 320 at a second end thereof, when the stent-graft is in the radially-expanded deployment state, and first longitudinal portion 350 extends to the first end of the stent-graft.

For some applications, as shown in FIG. 6G, first and second longitudinal portions 350 and 352 are non-longitudinally-overlapping. For these applications, first and second longitudinal portions 350 and 352 are typically longitudinally adjacent each other, as shown in FIG. 6G. Typically, first and second fabrics 356 and 358 are coupled to each other at a longitudinal junction 354 between first and second longitudinal portions 350 and 352, such as by suturing or stitching, so as to form a blood-tight seal between the first and second fabrics.

For other applications, as shown in FIG. 7, first and second longitudinal portions 350 and 352 are partially longitudinally overlapping along a longitudinally overlapping portion 370 of stent-graft 320. For these applications, the first and second fabrics 356 and 358 are coupled to each other at one or more locations 372 along longitudinally overlapping portion 370, such as by suturing or stitching, so as to form a blood-tight seal between the first and second fabrics. Typically, a length of longitudinally overlapping portion 370 is less than 5% of an overall length of the stent-graft, and/or is at least 2 mm, no more than 10 mm, and/or between 2 and 20 mm. For some applications, longitudinally overlapping portion 370 is positioned at a location along the stent-graft that has a diameter that is less than a greatest diameter of the stent-graft.

Reference is still made to FIGS. 6G and 8. For some applications, second endovascular stent-graft 322 comprises two different fabrics, as described above regarding endovascular stent-graft 320, optionally including any of the described variations in configuration (e.g., overlapping vs. non-overlapping).

For some applications, as described with reference to FIGS. 6A-G, second endovascular stent-graft 322 is a branching stent-graft, and endovascular stent-graft 320 is a main stent-graft, which is shaped so as to define a lateral opening 334. Second longitudinal portion 352 of branching stent-graft 322 is shaped so as to define an interface portion 374 configured to form a blood-tight seal with lateral opening 334 of main stent-graft 320. As mentioned above, the second material of second fabric 358 may comprise a less deformable material, such as polyester, which strengthens the interface between the stent-grafts, which is generally subject to greater stress than other portions of the stent-grafts. Optionally, first longitudinal portion 352 extends to a narrower end of the branching stent-graft, as described hereinabove regarding stent-graft 320.

These techniques described with reference to FIGS. 6G, 7, and 8 may be implemented in stent-graft systems that do not comprise distal restraining assembly 50, such as those stent-graft systems described in the patent applications incorporated by reference hereinbelow, or stent-graft systems known in the art.

Figure 9:
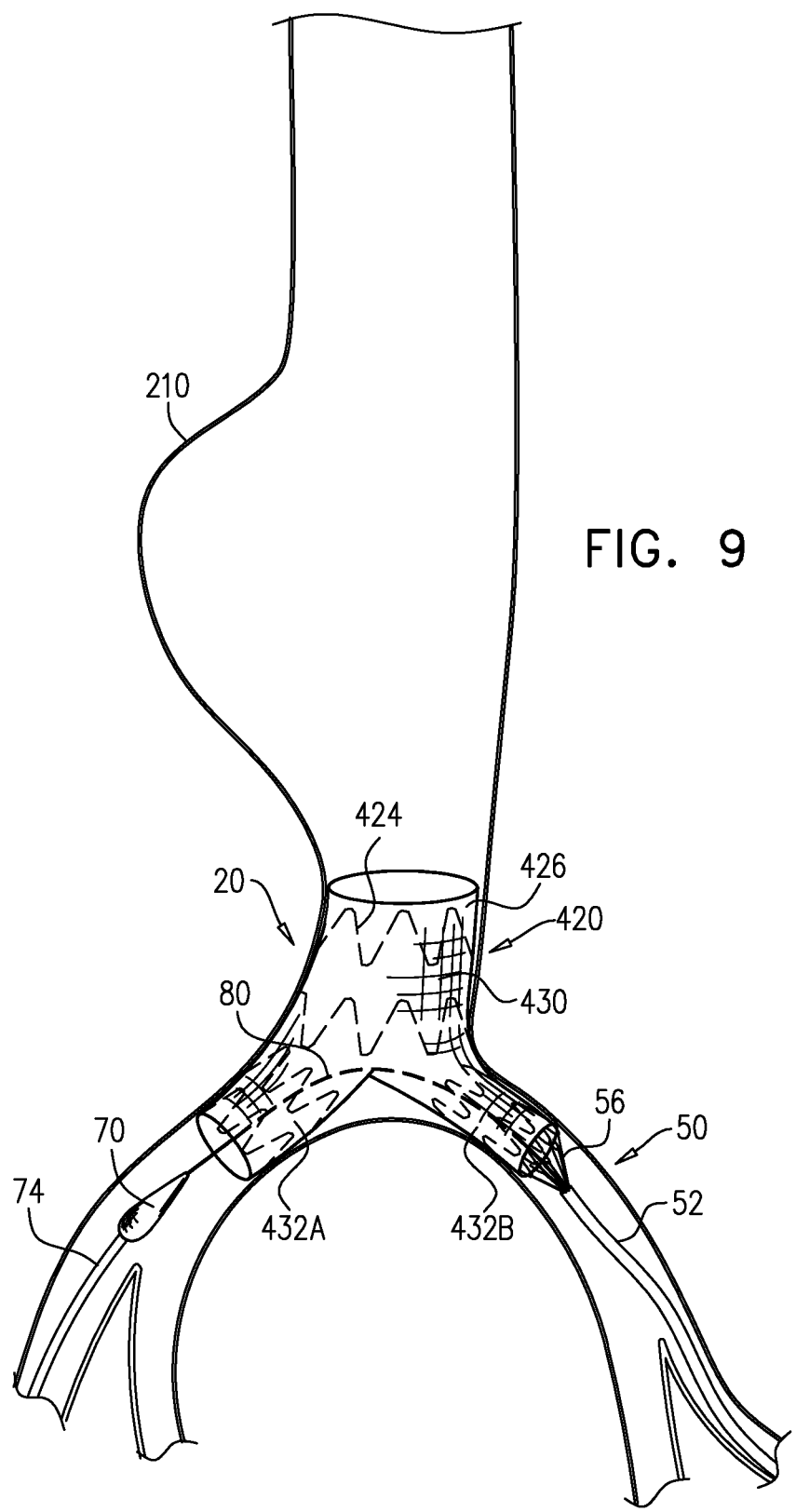
FIG. 9 is a schematic illustration of a bifurcated endovascular stent-graft, in accordance with an application of the present invention.

Reference is now made to FIG. 9, which is a schematic illustration of a bifurcated endovascular stent-graft 420, in accordance with an application of the present invention. In this configuration, endovascular implant 20 comprises bifurcated endovascular stent-graft 420, which comprises a stent member 424 and a fluid flow guide 426. Bifurcated endovascular stent-graft 420 is shaped so as to define a distal main lumen 430, which bifurcates into two proximal branching lumens 432A and 432B. For some applications, distal restraining assembly 50 is removably coupled to an end of one of the branching lumens, such as shown in FIG. 9.

For some applications, a length of a first one of the branching lumens is less than 90% of a length of a second one of the branching lumens. For some applications, the length of the first one of the branching lumens is at least 10% greater than the length of the second one of the branching lumens.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

PCT Application PCT/IL2008/000287, filed Mar. 5, 2008, which published as PCT Publication WO 2008/107885 to Shalev et al., and U.S. application Ser. No. 12/529,936 in the national stage thereof, which published as US Patent Application Publication 2010/0063575 to Shalev et al.

U.S. Provisional Application 60/892,885, filed Mar. 5, 2007

U.S. Provisional Application 60/991,726, filed Dec. 2, 2007

U.S. Provisional Application 61/219,758, filed Jun. 23, 2009

U.S. Provisional Application 61/221,074, filed Jun. 28, 2009

PCT Application PCT/IB2010/052861, filed Jun. 23, 2010, which published as PCT Publication WO 2010/150208

PCT Application PCT/IL2010/000564, filed Jul. 14, 2010, which published as PCT Publication WO 2011/007354

PCT Application PCT/IL2010/000917, filed Nov. 4, 2010, which published as PCT Publication WO 2011/055364

PCT Application PCT/IL2010/000999, filed Nov. 30, 2010, which published as PCT Publication WO 2011/064782

PCT Application PCT/IL2010/001018, filed Dec. 2, 2010, which published as PCT Publication WO 2011/067764

PCT Application PCT/IL2010/001037, filed Dec. 8, 2010, which published as PCT Publication WO 2011/070576

PCT Application PCT/IL2011/000135, filed Feb. 8, 2011, entitled, "Thermal energy application for prevention and management of endoleaks in stent-grafts," which published as PCT Publication WO 2011/095979

U.S. application Ser. No. 13/031,871, filed Feb. 22, 2011, entitled, "Flexible stent-grafts," which published as US Patent Application Publication 2011/0208289

U.S. Provisional Application 61/496,613, filed Jun. 14, 2011

U.S. Provisional Application 61/505,132, filed Jul. 7, 2011

U.S. Provisional Application 61/529,931, filed Sep. 1, 2011

PCT Application PCT/IL2012/000060, filed Feb. 2, 2012, which published as PCT Publication WO 2012/104842

PCT Application PCT/IL2012/000083, filed Feb. 16, 2012, which published as PCT Publication WO 2012/111006

PCT Application PCT/IL2012/000095, filed Mar. 1, 2012, which published as PCT Publication WO 2012/117395

PCT Application PCT/IL2012/000148, filed Apr. 4, 2012, which published as PCT Publication WO 2013/030818

PCT Application PCT/IL2012/000190, filed May 15, 2012, which published as PCT Publication WO 2013/171730, entitled, "Stent-graft with fixation elements that are radially confined for delivery"

U.S. patent application Ser. No. 13/523,296, filed Jun. 14, 2012, which issued as U.S. Pat. No. 8,574,287

PCT Application PCT/IL2012/000241, filed Jun. 19, 2012, which published as PCT Publication WO 2012/176187

PCT Application PCT/IL2012/000269, filed Jul. 2, 2012, which published as PCT Publication WO 2013/005207

PCT Application PCT/IL2012/050424, filed Oct. 29, 2012, which published as PCT Publication WO 2013/065040

PCT Application PCT/IL2012/050506, filed Dec. 4, 2012, which published as PCT Publication WO 2013/084235

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an endovascular stent-graft, which comprises:
    a flexible stent member; and
    a tubular fluid flow guide, which comprises:
        a first fabric, which comprises a first biologically-compatible substantially blood-impervious material, and which is attached to the stent member and extends along a first longitudinal portion of the tubular fluid flow guide; and
        a second fabric, which comprises a second biologically-compatible substantially blood-impervious material different from the first material, and which is attached to the stent member and extends along a second longitudinal portion of the tubular fluid flow guide, wherein the second longitudinal portion is at least partially non-longitudinally-overlapping with the first longitudinal portion,
    wherein the first and the second fabrics are coupled to each other by suturing or stitching,
    wherein the first material is less thrombogenic than the second material,
    wherein the stent-graft is configured to assume a radially-compressed delivery state and a radially-expanded deployment state,
    wherein the tubular fluid flow guide has first and second ends,
    wherein the first longitudinal portion is located along a narrower portion of the stent-graft than is the second longitudinal portion,
    wherein a perimeter of the tubular fluid flow guide at the first end is less than a perimeter of the tubular fluid flow guide at the second end, when the stent-graft is in the radially-expanded deployment state, and
    wherein the first longitudinal portion extends to the first end of the tubular fluid flow guide.

2. The apparatus according to claim 1, wherein the second material is less deformable than the first material.

3. The apparatus according to claim 1, wherein the first material comprises expanded polytetrafluoroethylene (ePTFE).

4. The apparatus according to claim 3, wherein the second material comprises a polyester.

5. The apparatus according to claim 1, wherein the second material comprises a polyester.

6. The apparatus according to claim 1, wherein the first and the second longitudinal portions are non-longitudinally-overlapping.

7. The apparatus according to claim 6, wherein the first and the second longitudinal portions are longitudinally adjacent each other.

8. The apparatus according to claim 7, wherein the first and the second fabrics are coupled to each other at a longitudinal junction between the first and the second longitudinal portions.

9. The apparatus according to claim 1, wherein the first and the second longitudinal portions are partially longitudinally overlapping along a longitudinally overlapping portion of the tubular fluid flow guide.

10. The apparatus according to claim 9, wherein the first and the second fabrics are coupled to each other at one or more locations along the longitudinally overlapping portion.

11. The apparatus according to claim 9, wherein the longitudinally overlapping portion of the tubular fluid flow guide has a length that is less than 5% of an overall length of the stent-graft.

12. The apparatus according to claim 9, wherein the longitudinally overlapping portion of the tubular fluid flow guide has a length of between 2 and 10 mm.

13. The apparatus according to claim 9, wherein the longitudinally overlapping portion of the tubular fluid flow guide is positioned at a location along the tubular fluid flow guide that has a diameter that is less than a greatest diameter of the stent-graft.

14. The apparatus according to claim 1, wherein the first end of the tubular fluid flow guide is configured to be positioned in a blood vessel that branches from an aortic arch, and the second end of the tubular fluid flow guide is configured to be positioned in a descending aorta.

15. Apparatus comprising an endovascular stent-graft, which comprises:
  a flexible stent member; and
  a tubular fluid flow guide, which comprises:
    a first fabric, which comprises a first biologically-compatible substantially blood-impervious material, and which is attached to the stent member and extends along a first longitudinal portion of the tubular fluid flow guide; and
    a second fabric, which comprises a second biologically-compatible substantially blood-impervious material different from the first material, and which is attached to the stent member and extends along a second longitudinal portion of the tubular fluid flow guide, wherein the second longitudinal portion is at least partially non-longitudinally-overlapping with the first longitudinal portion,
  wherein the first and the second fabrics are coupled to each other by suturing or stitching,
  wherein the second material is less deformable than the first material,
  wherein the stent-graft is configured to assume a radially-compressed delivery state and a radially-expanded deployment state,
  wherein the stent-graft has first and second ends,
  wherein the first longitudinal portion is located along a narrower portion of the stent-graft than is the second longitudinal portion,
  wherein a perimeter of the stent-graft at the first end is less than a perimeter of the stent-graft at the second end, when the stent-graft is in the radially-expanded deployment state, and
  wherein the first longitudinal portion extends to the first end of the stent-graft.

16. The apparatus according to claim 15, wherein the first material is less thrombogenic than the second material.

17. The apparatus according to claim 16, wherein the second material comprises a polyester.

18. A stent-graft system comprising the apparatus according to claim 15,
  wherein the stent-graft is a branching stent-graft,
  wherein the stent-graft system further comprises a main stent-graft, which is shaped so as to define a lateral opening, and
  wherein the second longitudinal portion of the branching stent-graft is shaped so as to define an interface portion configured to form a blood-tight seal with the lateral opening of the main stent-graft.

19. The apparatus according to claim 15, wherein the second material comprises a polyester.

20. A method comprising:
  providing an endovascular stent-graft, which includes (a) a flexible stent member, and (b) a tubular fluid flow guide, which includes (i) a first fabric, which comprises a first biologically-compatible substantially blood-impervious material, and which is attached to the stent member and extends along a first longitudinal portion of the tubular fluid flow guide, and (ii) a second fabric, which comprises a second biologically-compatible substantially blood-impervious material different from the first material, and which is attached to the stent member and extends along a second longitudinal portion of the tubular fluid flow guide, wherein the second longitudinal portion is at least partially non-longitudinally-overlapping with the first longitudinal portion, wherein the first and the second fabrics are coupled to each other by suturing or stitching, wherein the first material is less thrombogenic than the second material, wherein the first longitudinal portion is located along a narrower portion of the stent-graft than is the second longitudinal portion, wherein a perimeter of the tubular fluid flow guide at a first end thereof is less than a perimeter of the tubular fluid flow guide at a second end thereof when the stent-graft is in a radially-expanded deployment state, and wherein the first longitudinal portion extends to the first end of the tubular fluid flow guide; and
  implanting the stent-graft in vasculature of a patient by endovascularly introducing the stent-graft into the vasculature while the stent-graft is in a radially-compressed delivery state, and transitioning the stent-graft to the radially-expanded deployment state in the vasculature.

21. The method according to claim 20, wherein implanting the stent-graft in the vasculature comprises positioning the first end of the tubular fluid flow guide in a blood vessel that branches from an aortic arch, and the second end of the tubular fluid flow guide in a descending aorta.

* * * * *